US008877712B2

(12) United States Patent
Yang et al.

(10) Patent No.: US 8,877,712 B2
(45) Date of Patent: Nov. 4, 2014

(54) USE OF DEL-1 IN HAIR, BONE AND CARTILAGE REGENERATION

(75) Inventors: George P Yang, San Francisco, CA (US); Jonathan A. Mathy, Boston, MA (US); Thomas Quertermous, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1259 days.

(21) Appl. No.: 11/697,645

(22) Filed: Apr. 6, 2007

(65) Prior Publication Data

US 2007/0248641 A1 Oct. 25, 2007

Related U.S. Application Data

(63) Continuation-in-part of application No. PCT/US2005/036361, filed on Oct. 11, 2005.

(60) Provisional application No. 60/617,898, filed on Oct. 11, 2004.

(51) Int. Cl.
| | | |
|---|---|---|
| *A61P 19/02* | (2006.01) | |
| *A61K 38/02* | (2006.01) | |
| *A61K 38/16* | (2006.01) | |
| *A61K 38/18* | (2006.01) | |
| *A61K 31/7084* | (2006.01) | |
| *A61L 27/38* | (2006.01) | |
| *A61K 38/30* | (2006.01) | |
| *A61K 9/00* | (2006.01) | |

(52) U.S. Cl.
CPC ............. *A61K 38/18* (2013.01); *A61K 38/1841* (2013.01); *A61K 31/7084* (2013.01); *A61L 27/3817* (2013.01); *A61L 27/3847* (2013.01); *A61L 2300/252* (2013.01); *A61L 27/3852* (2013.01); *A61K 38/30* (2013.01); *A61K 9/0024* (2013.01); *A61K 27/54* (2013.01); *A61L 2300/414* (2013.01)
USPC ....... 514/16.8; 514/17.1; 514/18.9; 514/19.1; 514/21.2

(58) Field of Classification Search
None
See application file for complete search history.

(56) References Cited

U.S. PATENT DOCUMENTS

| | | | |
|---|---|---|---|
| 5,877,281 A | 3/1999 | Quertermous et al. | |
| 2003/0077821 A1* | 4/2003 | Sah et al. | 435/366 |
| 2003/0114936 A1* | 6/2003 | Sherwood et al. | 623/23.58 |
| 2003/0185794 A1 | 10/2003 | Colley | |
| 2003/0219875 A1 | 11/2003 | Rosen et al. | |
| 2004/0166100 A1* | 8/2004 | Elia | 424/93.21 |

OTHER PUBLICATIONS

Solomon, L., J. Bone Joint Surg. Br., 1976, vol. 58-B(2):176-183.*
Aoka, et al.; "The Embryonic Angiogenic Factor Del1 Accelerates Tumor Growth by Enhancing Vascular Formation," Microvascular Research 64, 148-161 (2002).
Aoki, et al.; "Expression of Developmentally regulated endothelial Cell Locus 1 Was Induced by Tumor-Derived Factors Including VEGF," Biochemical and Biophysical Research Communications 333, 990-995 (2005).
Boudreau, et al.; "The Homeobox Transcription Factor Hox D3 Promotes Integrin α5β1 Expression and Function during Angiogenesis," The Journal of Biological Chemistry; vol. 279, No. 6, 4862-4868 (2004).
Chen, et al.; "A Fibrous-Bed Bioreactor for Continuous Production of Developmental Endothelial Locus-1 by Osteosarcoma Cells," Journal of Biotechnology 97, 23-39 (2002).
Deng, et al.; "Study on the Three-Dimensional Proliferation of Rabbit Articular Cartilage-Derived Chondrocytes on Polyhydroxyalkanoate Scaffolds," Biomaterials 23, 4049-4056 (2002).
Egermann, et al.; "The Potential of Gene Therapy for Fracture Healing in Osteoporosis," International Osteoporosis 16:S120-S128 (2005).
Hanayama, et al.; "Expression of Developmental Endothelial Locus-1 in a Subset of Macrophages for Engulfment of Apoptic Cells," the Journal of Immunology 172:3876-3882 (2004).
Hidai, et al.; "Cloning and Characterization of Developmental Endothelial Locus-1: An Embryonic Endothelial Cell Protein That Binds the αvβ3 Integrin Receptor," Genes and Development 12:21-33 (1998).
Ho, et al.; "Developmental Endothelial Locus-1 (Del-1), a Novel Angiogenic Protein: Its Role in Ischemia," Circulation 109:1314-1319 (2004).
Internet Article: U.S. Food and Drug Administration—Department of Health and Human Services—Center for Devices and Radiological Health (Consumer Information); "New Device Approval: Infuse® Bone Graft—P000054;" http://www.fda.gov/cdrh/mda/docs/p000054.html; Oct. 11, 2005.
Ishida, et al.; "Endothelial Lipase is a Major Determinant of HDL Level;" The Journal of Clinical Investigation 111:347-355 (2003).
Kown, et al.; "Comparison of Developmental Endothelial Locus-1 Angiogenic Factor With Vascular Endothelial Growth Factor in a Porcine Model of Cardiac Ischemia;" Ann Thorac Surg; 76:1246-1251 (2003).
Parikh; "Bone Graft Substitutes: Past, Present, Future;" Journal of Postgraduate Medicine; 48:142-148 (2002).
Penta, et al.; "Del1 Induces Integrin Signaling and Angiogenesis by Ligation of αvβ3;" The Journal of Biological Chemistry; 274:11101-11109 (1999).
Pfister, et al.; "Del1: A New Protein in the Superficial Layer of Articular Cartilage;" Biochemical and Biophysical Research Communications; 286:268-273 (2001).
Quezada, et al.; "Biodistribution and Safety Studies of hDel-1 Plasmid-Based Gene Therapy in Mouse and Rabbit Models;" Journal of Pharmacy and Pharmacology; 56:177-185 (2004).
Raghavachari, et al.; "Targeted Gene Delivery to Skin Cells in Vivo: A Comparative Study of Liposomes and Polymers as Delivery Vehicles;" Journal of Pharmaceutical Sciences; 91:615-622 (2002).

(Continued)

*Primary Examiner* — Xiaozhen Xie
(74) *Attorney, Agent, or Firm* — Thomas|Horstemeyer, LLP

(57) ABSTRACT

Methods and compositions are described enhancing bone density or formation, including for stabilizing bone grafts, bone repair, joint replacement, and cartilage repair that includes providing a composition including Del-1 locally to a site for enhancing bone density or formation, or to a culture or chondrocytes or multipotent chondrocyte precursor cells, whereby survival or differentiation of chondrocytes at the site is enhanced, thereby ultimately enhancing bone density or formation. Methods and compositions for stimulating hair regrowth are also provided.

7 Claims, 11 Drawing Sheets

(56) References Cited

OTHER PUBLICATIONS

Rajagopalan, et al.; "Trial Design Paper: Design of the Del-1 for Therapeutic Angiogenesis Trial (DELTA-1), a Phase II Multicenter, Double-Blind, Placebo-Controlled Trial of VLTS-589 in Subjects with Intermittent Claudication Secondary to Peripheral Arterial Disease;" Human Gene Therapy 15:619-624 (2004).

Rezaee, et al.; "Del1 Mediates VSMC Adhesion, Migration, and Proliferation Through Interaction with Integrin $\alpha v\beta 3$;" Am J Physiol Heart Circ Physiol 282:H1924-H1932 (2002).

Saito, et al.; "High Efficiency Genetic Modification of Hair Follicles and Growing Hair Shafts;" Proceedings of the National Academy of Sciences of the United States of America; 99:13120-13124 (2002).

Shou, et al.; "Robust Generation of New Hair Cells in the Mature Mammalian Inner Ear by Adenoviral Expression of Hath1;" Molecular and Cellular Neuroscience 23:169-179 (2003).

Sinha, et al.; "Defining the Reculatory Factors Required for Epidermal Gene Expression," Molecular and Cellular Biology; 20:2543-2555 (2000).

Sinha, et al.; "Identification and Dissection of an Enhancer Controlling Epithelial Gene Expression in Skin," Proceedings of the National Academy of Sciences of the United States of America; 98:2455-2460 (2001).

Xu, et al.; "Evaluation of Different Scaffolds for BMP-2 Genetic Orthopedic Tissue Engineering," Journal of Biomed Mater Res B Appl. Biomater 758:289-303 (2005).

Zelzer, et al.; "VEGFA is Necessary for Chondrocyte Survival During Bone Development," Development 131:2161-2171 (2003).

Malladi, et al.; "The Role of Developmental Endothelial Locus 1 (Del1) in Skeletal Development," Journal of the American College of Surgeons, 199:S49-S50 (2004).

Hsu, et al.; "Increased Rate of Hair Regrowth in Mice with Constitutive Over Expression of the Angiogenic Factor Del1 in Basal Keratinocytes," Journal of the American College of Surgeons 199:S63 (2004).

International Search Report received in corresponding PCT Application No. PCT/US2005/036361 (International Publication No. WO 2006/042197 A3) dated Aug. 28, 2006.

* cited by examiner

USE OF DEL-1 IN HAIR, BONE AND CARTILAGE REGENERATION

CROSS REFERENCE TO RELATED APPLICATIONS

This application is a continuation-in-part of, and claims priority to PCT/US2005/036361, filed Oct. 11, 2005 (published as WO2006/042197), which claimed priority to U.S. Provisional Application Ser. No. 60/617,898 filed Oct. 11, 2004.

FIELD OF THE INVENTION

This invention relates compositions and methods for regeneration of hair, bone and cartilage using a Del-1 as a growth factor.

BACKGROUND OF THE INVENTION

Without limiting the scope of the invention, its background is described in connection with novel compositions and methods for enhancement of skeletal fracture healing, in the tissue engineering, and for therapeutic hair regeneration using Developmentally Regulated Endothelial Locus 1 (Del-1) genes and proteins as essential growth factors.

Del-1 is a secreted extracellular matrix protein that has been shown to be an angiogenic factor. Del-1 protein expressed in a recombinant baculovirus system was shown to promote $\alpha v\beta 3$-dependent endothelial cell attachment and migration. Attachment of endothelial cells to Del-1 was associated with clustering of the integrin $\alpha v\beta 3$, the formation of focal complexes, and recruitment of talin and vinculin into these complexes followed by downstream kinase signaling. When recombinant Del-1 was evaluated in an in ovo chick chorioallantoic membrane (CAM) assay, it was found to have potent angiogenic activity. (Penta K, et al. *J Biol Chem.* 274 (16) (1999) 11101-9). Importantly, neutralizing antibody to Del-1 or mutation of the RGD motif will inhibit this angiogenic activity. Thus, Del-1 is a secreted extracellular matrix protein that is capable of stimulating angiogenesis through integrin binding.

The full length human and murine Del-1 protein of 480 amino acids has three Notch-like epidermal growth factor repeats, an RGD motif, and two discoidin domains. (Hidai C, et al. *Genes Dev.* 12(1) (1998) 21-33). During embryogenesis, Del-1 is spatiotemporally expressed during embryogenesis prominently in the developing vasculature, portions of the brain, and in cartilaginous structures. In the early Hidai study, expression of Del-1 was also noted in endochondral bone of 9.5 day mouse embryos as well as the hypertropic chondrocytes of limb bones and vertebral bodies. By 13.5 days, Del-1 expression in endothelial type cells ceased although expression of Del-1 in hypertropic chondrocytes was retained. Although considered possible that Del-1 was directly involved in supporting bone function, it was thought to be a more attractive hypothesis that expression of Del-1 by chondrocytes reflected a mechanism by which these cells regulate vascularization of bone-forming regions. No Del-1 was found to be expressed in adult tissues.

Subsequently, Del-1 was found to be present in adult articular cartilage in the cell-associated matrix of freshly isolated superficial chondrocytes and was thought to interact with integrin $\alpha v\beta 3$, which is present in the superficial layer of articular cartilage. (Pfister, et al. *Biochemical and Biophysical Research Communications* 286 (2001) 268).

Bone fracture is a very common wound experienced by virtually all persons at some time in their lives. It is estimated that 5-10% of all fractures show impaired healing, leading to delayed or non-union. Thus, chemical or physical methods to accelerate bone healing are of great interest. As with soft tissue wound healing, fracture healing progresses through three general stages: inflammation, proliferation, and remodeling. However, because of supporting strength needed in bone, fractures generally take longer to heal than soft tissue wounds. New bone forms through a cartilaginous intermediate, which can be seen by x-ray about 10 days after fracture. The cartilage is soft and flexible and takes weeks to months for replacement with hard bony tissue. Weight supporting long bones, such as the femur, can take 3-5 months to heal. Healing requires immobilization of the fracture and is associated with considerable morbidity.

Growth factors have been studied in an effort to augment fracture healing with various results. The growth factors IGF-1 and TGF-$\beta 1$ are known to stimulate fracture healing including through an earlier appearance of cartilage and an enhanced maturation of the callus tissue. (Wildmann B et al. *J Biomed Mater Res B Appl Biomater* 65(1)(2003) 150-6). Osteosynthetic implants including growth factors have yielded some encouraging results in animal studies. Thus, implants composed of poly(D,L-lactide) (PDLLA) impregnated with insulin-like growth factor-1 (IGF-1) have been reported to accelerate fracture healing significantly. (Schmidmaier et al. *Bone* 28(4) (2001) 341-50). Likewise, a mineralized collagen matrix combined with recombinant human growth and differentiation factor-5 in a rabbit posterolateral spinal fusion model resulted in biomechanical strength of treated motion segments that was not statistically different from an autograft suggesting an effective alternative to autograft for bone grafting procedures. (Spiro et al. *Anat Rec* 263(4) (2001) 388-95).

Bone morphogenetic protein-2 (BMP-2) has been reported to increase the rate of callous formation without affecting the amounts of bone or cartilage ultimately produced. (Bax BE et al. *Calcif Tissue Int* 65(1) (1999) 83-9). In a large animal study, injection of osteogenic protein-1 (BMP-7) into the fracture gap was associated with higher stiffness and strength 2 weeks after injection. (Blokhuis T J, et al. *Biomaterials* 22(7) (2001) 725-30). A human randomized, controlled, single-blind clinical trial in open tibial shaft fractures has been conducted in which a recombinant human BMP-2 implant (rhBMP-2 applied to an absorbable collagen sponge) was placed over the fracture at the time of definitive wound closure. Use of rhBMP-2, albeit at large doses, was significantly superior to control in reducing the frequency of secondary interventions and overall invasiveness of the procedures, accelerating fracture and wound-healing, and reducing the infection rate in patients with an open fracture of the tibia. (Govender S et al. *J Bone Joint Surg Am* 84-A(12) (2002) 2123-34). Similarly, a human anterior lumbar fusion clinical trial has comparing rhBMP-2 on an absorbable collagen sponge (INFUSE® Bone Graft) with use of an autograft transferred from the iliac crest implanted in a fusion device. The patients treated with rhBMP-2 had statistically superior outcomes with regard to length of surgery, blood loss, hospital stay, re-operation rate, median time to return to work, and fusion rates at 6, 12, and 24 months. Burkus J K et al. *J Spinal Disord Tech* 16(2) (2003) 113-22. In 2004, the FDA granted pre-market approval P000054 for use of the INFUSE® rhBMP-2 collagen sponge in treating acute, open tibial shaft fractures that have been stabilized with intermedullary nail fixation. However, the FDA new device approval overview notes that use of the INFUSE® device caused fractures to heal in a similar manner to bones not treated with the device. Patients who received INFUSE® required fewer interventions to promote healing compared to patients who did not receive the device, however, patients who received the device and required an intervention healed at a slower rate compared to patients who did not receive the device.

The utility of TGF-beta in bone healing has been conflicting (Tielinen et al. *Arch Orthop Trauma Surg* 121(4) (2001) 191-6). Fibroblast growth factor (FGF) has a capacity to enlarge the cartilaginous calluses, but not to induce more rapid healing (Nakajima et al. *J Orthop Res* 19(5) (2001) 935-44). There remains a need for further growth factors that are able to accelerate the rate of events in early fracture healing including bone grafting.

Tissue disease and organ failure leads to an estimated 8 million surgical procedures annually in the United States. Treatments in the form of transplantation and tissue reconstruction are among the most expensive, costing billions of dollars a year. Tissue engineering using biodegradable scaffolds impregnated with growth factors or autologous cells that are able to populate the scaffold is a promising technique for the generation of replacement cartilaginous tissues including nasal septum, ear, throat, and the cartilage lining the joints ("articular cartilage").

A major problem faced by the aging population is osteoarthritis (OA). See Felson D T. Clinical practice. Osteoarthritis of the knee. *N Engl J Med* 354(8) (2006) 841-8. Cartilage serves as a cushion for the impact of locomotion and excessive wear at joint surfaces leads to loss of the articular cartilage with ensuing inflammation and pain. The only reliable method to ease pain in these patients is a total joint replacement, a major procedure with significant risks for morbidity and mortality. Cartilage has a very limited ability to regenerate over time so there is no appreciable replacement of cartilage lost to OA. Cartilage has limited capacity for self-repair due in part to a poor blood supply. Articular cartilage, is particularly difficult to repair due to an isolated chondrocyte (cartilage-producing cell) microenvironment, as well as high forces generated in the joint. Over the long term, defects may progress to end stage arthritis, leading to the need for joint replacement. A popular dietary supplement that has been purported to aid OA is glucosamine and chondroitin sulfate. A recent study has just demonstrated that there is no significant benefit of these supplements in chronic disease, but the volume of sales of the supplements suggests the extent of this disease and the numbers of people seeking relief from pain related to it. See Clegg D O, Reda D J, Harris C L, et al. Glucosamine, chondroitin sulfate, and the two in combination for painful knee osteoarthritis. *N Engl J Med* 2006; 354(8):795-808.

One solution to repair of cartilaginous tissue is to administer autologous chondrocytes in combination with novel synthetic scaffolds to provide immediate structural repair as well as a new population of cells capable of growing new cartilaginous tissue. There is currently one approved tissue engineered cartilage that is used for this purpose (Carticel, Genzyme, Cambridge, Mass.). This therapy has suffered from several problems. The patient must not only endure the harvesting of autologous chondrocyte donor tissue, but must wait for proliferation of these cells in vitro prior to implantation. There is potential morbidity from the donor site required to acquire autologous chondrocytes, weeks are required for expansion of to create a small construct, many of these grafts disintegrate after implantation, and finally, the costs of this therapy are extremely high. What is needed is a factor able to enhance the in vitro populating of scaffolds or, alternatively, the recruitment and growth potentiation of chondrocytes to the scaffold in vivo by impregnating the scaffold with a chondrocyte growth factor. What is further needed is a more readily available source of donor cells.

Another approach to managing OA is to prevent early disease from worsening. A concept that has been emerging over the past decade has been the role of apoptosis in the pathogenesis of OA. It has been well documented that articular injury through trauma or chronic impaction leads to death of the articular cartilage. More recently, multiple studies have shown increased rates of apoptosis in joints that have suffered trauma. These studies have suggested that affecting chondrocyte apoptosis may be a method to preventing development of OA following injury to the articular cartilage or the progression of OA after it has initially manifested, but before the development of severe disease. What is need is an inhibitor of chondrocyte apoptosis such that loss of cartilage can be controlled.

Another therapeutic need is for a viable hair regrowth compositions and methods. Hair loss on the scalp can be a consequence of aging, hormonal changes, exposure to certain drugs, and/or a family history of baldness. Hair replacement surgery, which is the only permanent hair replacement option, requires either invasive skin flap surgery or autologous grafts. The only available medical therapies are with the topical drug minoxidil (brand name Rogaine®) or the oral medication finasteride (brand name Propecia®), each of which take up to 6 months of treatment before it can be apparent whether the drugs will work. Further therapies for hair regrowth are needed.

BRIEF SUMMARY OF THE INVENTION

In the present studies to examine its effect on bone and skin wound healing, it was found by the present inventors that a primary effect of Del-1 is enhancement of hair re-growth. In addition, Del-1 was found to be involved in chondrocyte growth as well as differentiation of chondrocytes from multipotent cells and to have a role in the healing of fractures. Indeed, present evidence indicates that Del-1 has a role in reducing or preventing apoptosis of chondrocytes. Furthermore, Del-1 up-regulation is shown to be associated with the in vitro differentiation of adipose derived mesenchymal stem cells (AdMSCs) into cartilage, thus supporting use in providing a more accessible source of cells for transplantation and repair and in the tissue engineering of cartilage.

Thus, in one embodiment of the invention a method is provided for enhancing bone density or formation, including for stabilizing bone grafts, bone repair and joint replacement, that includes providing a composition including Del-1 locally to a site for enhancing bone density or formation, whereby survival or differentiation of chondrocytes at the site is enhanced, thereby ultimately enhancing bone density or formation.

In one embodiment, the Del-1 containing composition comprises a carrier for prolonged release of Del-1 locally at the site for enhancing bone density or formation. The carrier may be one or more of materials including structural scaffold materials, nonstructural semi-fluid materials such as gels and viscous polymers, resorbable carrier materials such as collagen sponges, demineralized bone matrix compositions, and autologous bone. All of these materials are able to provide for prolonged release of Del-1 during healing.

In one embodiment of the invention, the Del-1 containing composition further comprises one or more additional growth factors for promoting growth and regeneration of bone. Additional agents that may be utilized include transforming growth factor (TGF-β), bone morphogenic proteins (BMPs), fibroblast growth factors (FGFs), insulin-like growth factors (IGFs), platelet-derived growth factors (PDGFs), and vascular endothelial growth factors (VEGFs).

The Del-1 can be provided as a protein or, alternatively, as a gene expression construct that encodes a Del-1 protein and drives expression of Del-1 protein from cells that take up the gene construct at the site. The Del-1 protein or gene can be provided by a number of methods including by direct administration to the site for enhancing bone formation, either unformulated, formulated in a pharmaceutically compatible solution, or incorporated in a biomaterial such as, for example, a matrix, hydrogel, polymer, tissue scaffold, demineralized bone matrix or cellular support. In one embodiment of the present invention, the site for enhancing bone density or formation is a bony fracture and/or region surrounding a bony fracture.

In one embodiment of the invention, a method is provided for preparing biomaterials including treated tissue scaffolds for enhanced growth of chondrocytes, by adding Del-1 to the scaffold in sufficient quantities to enhance growth of chondrocytes that populate the Del-1 treated tissue scaffold. The scaffold can be treated with a composition including Del-1 and then directly implanted such that the scaffold is populated with chondrocytes and/or chondrocyte precursors after implantation. Alternatively, the scaffold can be populated with autologous chondrocytes and/or chondrocyte precursors in vitro prior to implantation. In one embodiment, the autologous chondrocytes are derived from multipotent cells isolated from one or more tissues selected from the group consisting of fat bone marrow, synovium, periosteum, and skeletal muscle.

In one embodiment, the Del-1 protein or encoding nucleic acid is incorporated into the materials forming the scaffold as it is manufactured, such as, for example, by crosslinking a polymer solution in a prosthesis mold and adding the Del-1 to the polymer solution prior to crosslinking. Alternatively, the scaffold can be preformed and then treated with Del-1 or Del-1 encoding nucleic acids.

The findings presented here are directly adaptable to treatment of disease. Thus, in one embodiment of the invention, Del-1 is employed in vivo in preventing apoptosis of chondrocytes and thus the progression of OA. To this end, in one embodiment of the invention, Del-1 is administered to a patient as an injection of Del-1 protein, either in native form or as modified to prolong in vivo half-life, such as for example by pegylation. Alternatively, in other embodiments, Del-1 is delivered by gene therapy. With the gene therapy delivery, Del-1 is generated in situ by the patient's own cells subsequent to delivery of a gene vector functionally encoding Del1 to a site in the body where OA is active. Del-1 delivered in such a way by gene therapy enables prolonged local exposure from each injection of the vector.

In other embodiments of the invention, Del-1 is employed in cartilaginous differentiation of multipotent cells for the surgical repair of OA lesions by implantation of cartilaginous grafts that are generated by in vitro culture of autologous AdMSC in differentiation media containing Del-1.

In another embodiment of the invention, a method for enhancing the re-growth of hair cells is provided including providing Del-1 to a site for re-growth of hair cells. The Del-1 can be provided as a protein or as a nucleic acid encoding and expressing Del-1.

BRIEF DESCRIPTION THE DRAWINGS

For a more complete understanding of the present invention, including features and advantages, reference is now made to the detailed description of the invention along with the accompanying figures:

FIG. 1 illustrates the time course of Del-1 expression in an acute wound microenvironment in vitro.

FIGS. 2A and B are photographs representing Del-1 transcriptional activity during development as reflected by LacZ staining, which appears blue and appears as a darker grey when reproduced in black and white.

FIG. 3A is a photograph facial whisker (vibrissae) of follicles in transgenic mice expressing LacZ under the expression control of Del-1 regulatory regions, while 3B is staining of wild type vibrissae. The LacZ staining, which appears blue and appears as a darker grey when reproduced in black and white.

FIGS. 4A-D depicts the 2-6 wk time course of changes in callous volume on the basis of 3D CT reconstruction following tibial fracture repair in wild type mice versus Del-1 knockout mice.

Figure 11:
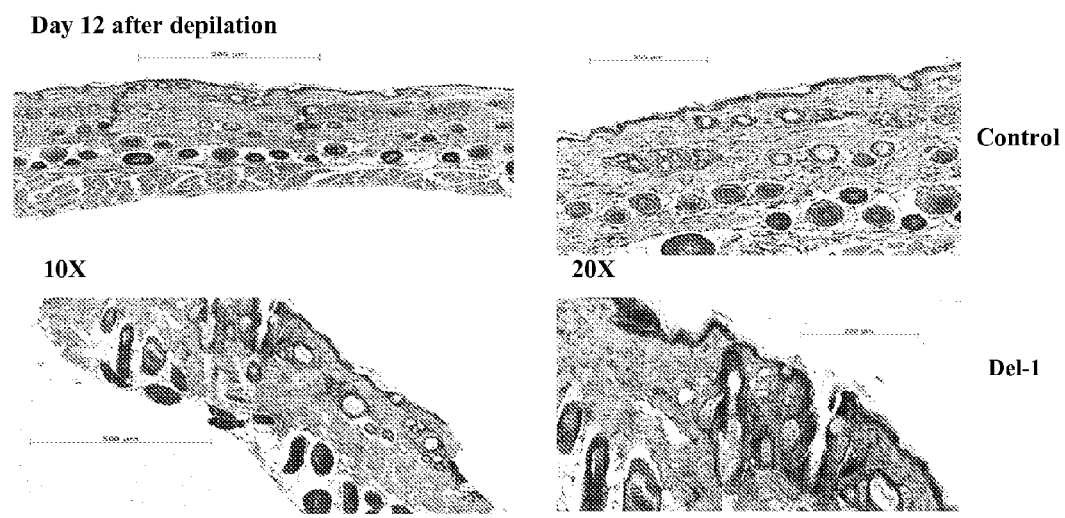

FIG. 11 represents the 10× and 20× magnifications of histology of skin of wild type mice that were depilated and then treated with Del-1 protein injections. The top two panels represent control injections while the bottom two panels represent the results of Del-1 protein injections at day 12.

Figure 12A:
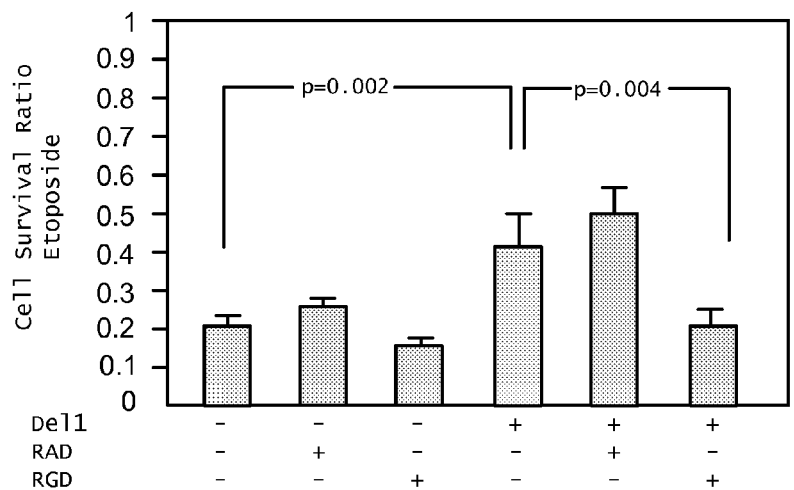
Figure 12B:
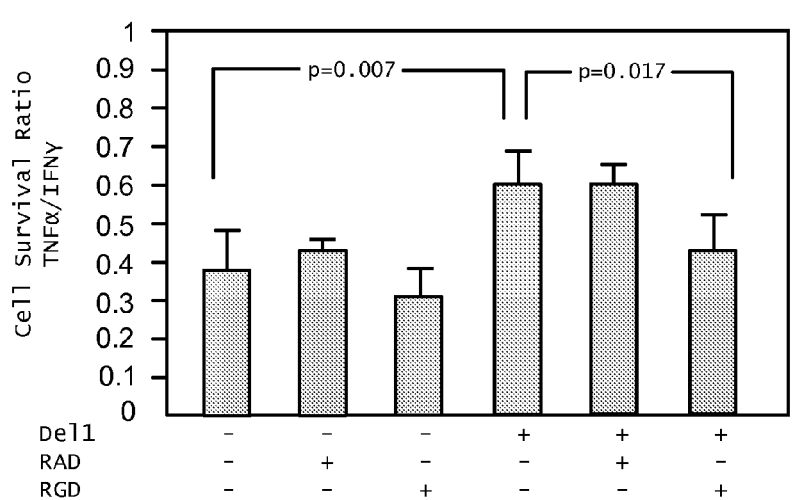
Figure 12C:
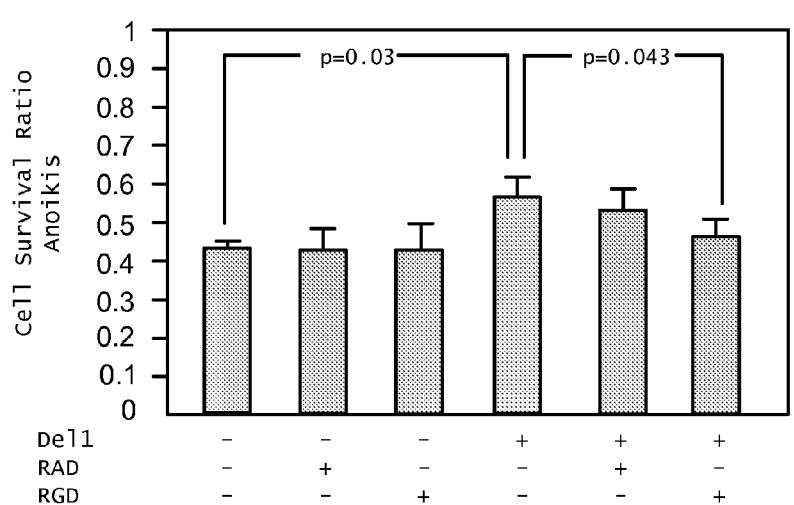

FIGS. 12A-C depict the results of studies to determine the role of the Del-1 RGD motif in its anti-apoptotic effect in endothelial cells. HUVECs were assayed for cell survival by WST-8 assay following apoptotic stimuli with etoposide (FIG. 12A), TNF-α/IFNγ (FIG. 12B), or anoikis (FIG. 12C) with or without Del1.

Figure 13A:
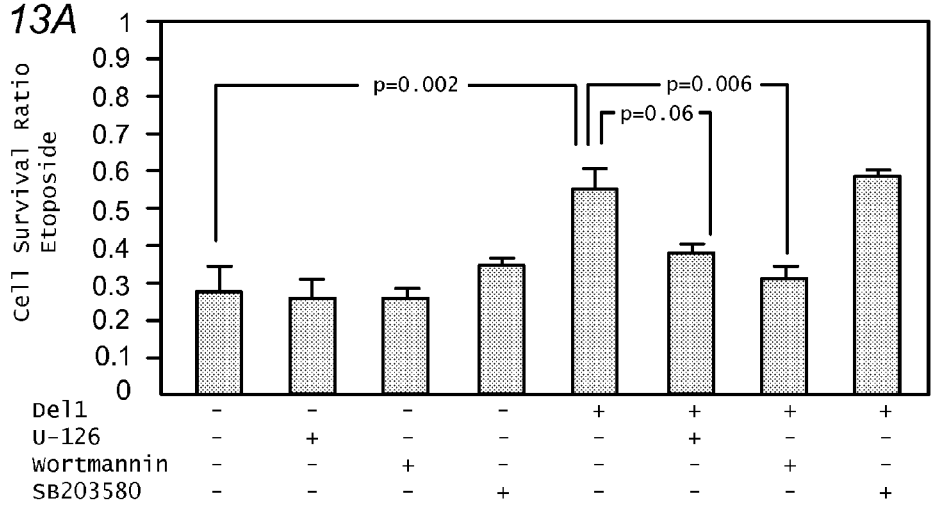
Figure 13B:
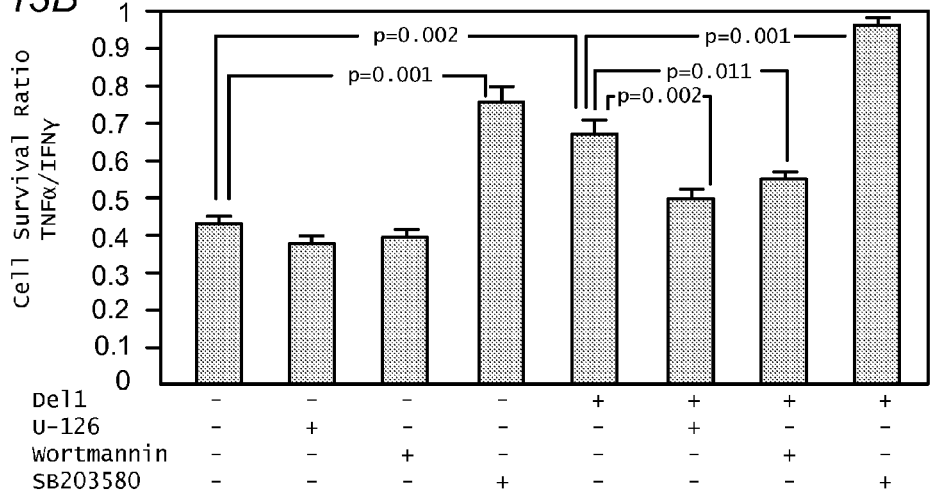
Figure 13C:
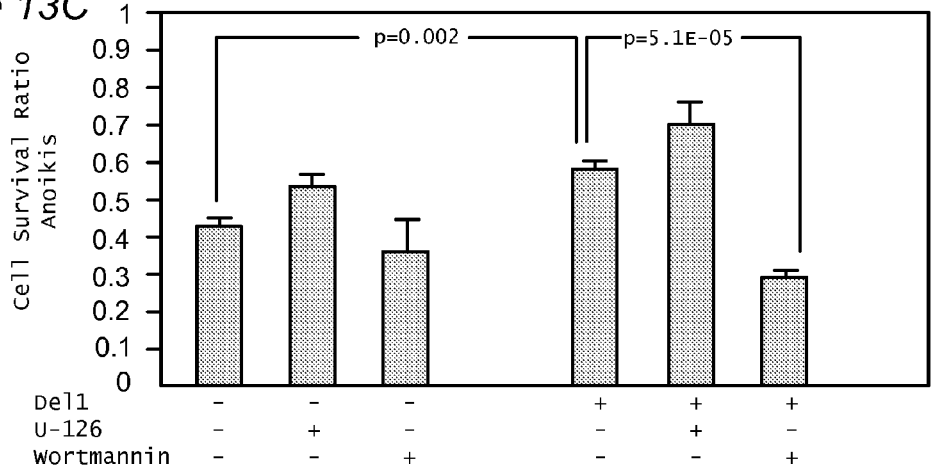

FIGS. 13A-C depict the results of studies to confirm the role of FAK/ERK and PI3/Akt signaling in mediating the anti-apoptotic effect of Del-1 in HUVEC cells due to etoposide (FIG. 13A), TNF-α/IFNγ (FIG. 13B), or anoikis (FIG. 13C).

Figure 14:
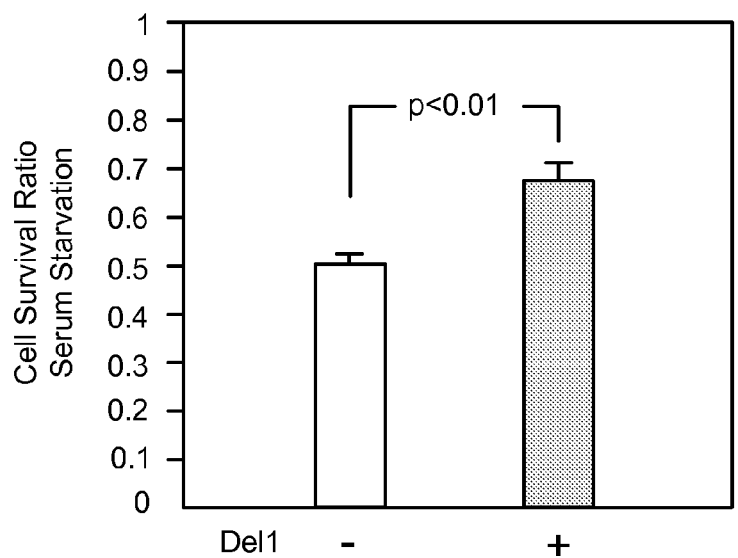
Figure 14:
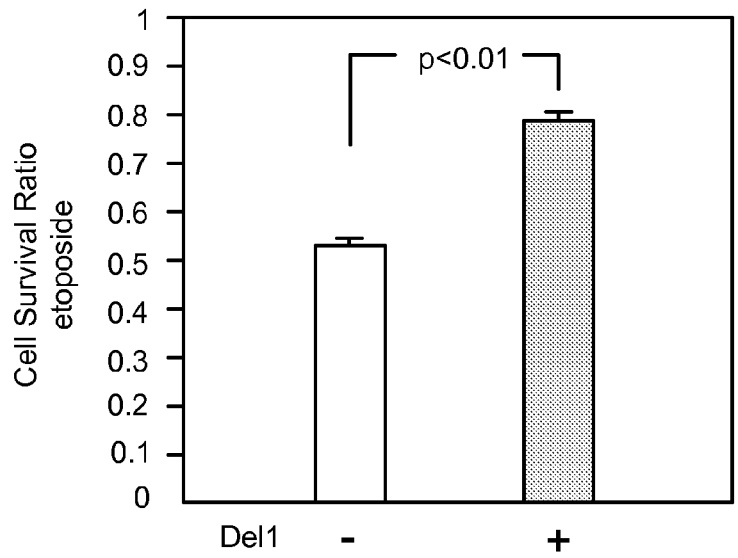

FIGS. 14 A-C depict the results of studies to determine a role for Del-1 in preventing apoptosis of chondrocytes. Primary human chondrocytes were assayed for apoptosis due to serum starvation (FIG. 14A), etoposide (FIG. 14B), and anoikis (FIG. 14C) in the presence or absence of Del1.

Figure 15:
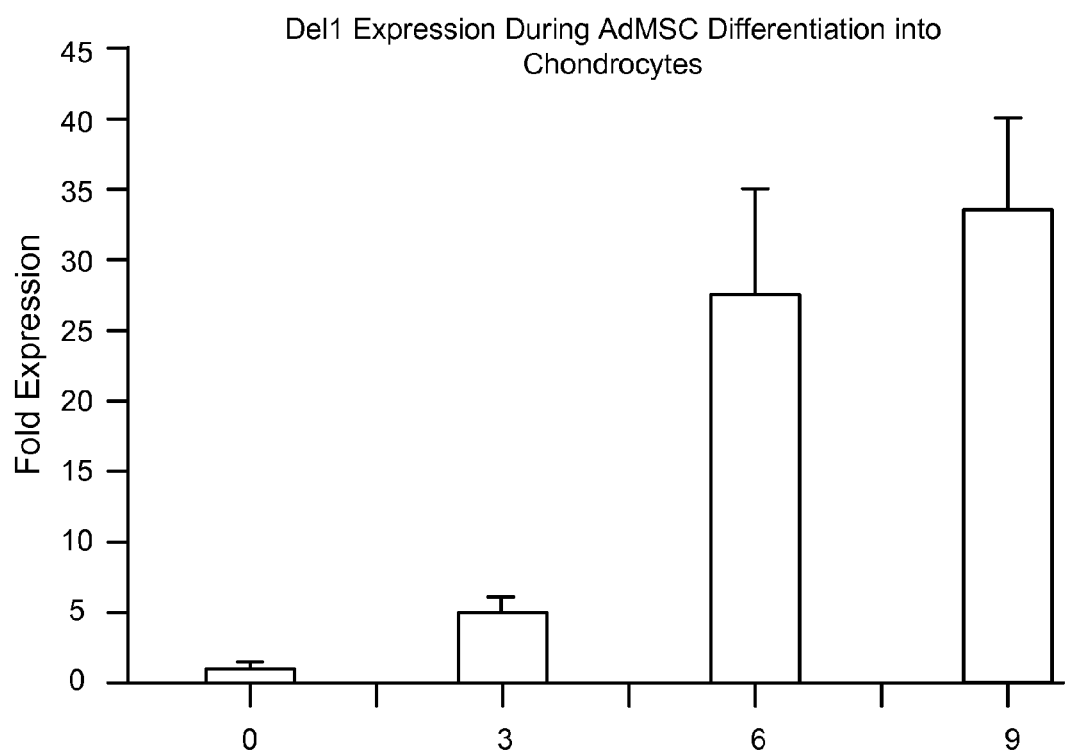

FIG. 15 depicts upregulation of Del-1 in AdMSCs harvested from wild type mice placed into chondrogenic medium.

DETAILED DESCRIPTION OF THE INVENTION

While the making and using of various embodiments of the present invention are discussed in detail below, it should be appreciated that the present invention provides many applicable inventive concepts which can be employed in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein "Del-1" refers to Developmentally Regulated Endothelial Locus 1 proteins and gene materials encoding and expressing Del-1 proteins, as well as fragments of Del-1 that are able to promote the growth of chondrocytes, cartilage and hair. Del-1 is presently identified in the Online Mendelian Inheritance in Man (OMIM-entry #606018) as "EGF-Like Repeats- and Discoidin I-Like Domains-Containing Protein 3 (EDIL3)". The reference sequence for the human 480 aa protein is Accession No. NP_005702 GI:31317224. The reference sequence for the 2974 base pair human mRNA is Accession No. NM_005711.3 GI:31317223. The provisional reference sequence for the corresponding murine sequence is NM_010103.1 GI:46879189.

Del-1 was initially described as a gene whose expression was highly associated with vasculogenesis. During development, it was expressed in the developing vasculature and endocardium of the heart. See Hidai C, et al. *Genes Dev* 1998; 12(1):21-33. However, there is no apparent defect in the vasculature or heart of the Del-1 null mutant mouse. It was also expressed in the developing vertebrae. More recently, another group has noted expression of Del-1 in articular cartilage. Pfister B E, Aydelotte M B, Burkhart W, et al. Del-1: a new protein in the superficial layer of articular cartilage *Biochem Biophys Res Commun* 286(2) (2001) 268-73.

Del-1 is a member of an emerging family of secreted proteins based upon shared protein sequence similarity. Milk fat globule epidermal growth factor 8 (MFG-E8) was originally described by a group studying the protein composition of breast milk fat. Another group independently purified MFG-E8 based upon its ability to enhance the phagocytosis of apoptotic cells by macrophages. Hanayama R, Tanaka M, Miyasaka K, et al. Autoimmune disease and impaired uptake of apoptotic cells in MFG-E8-deficient mice *Science* 304 (5674) (2004) 1147-50.

MFG-E8 recognizes aminophospholipids in apoptotic cells and attracts phagocytes through its RGD motif. The RGD sequence interacts with integrin $\alpha_v\beta_3$ on the phagocytes and brings them into proximity with the apoptotic cell so they can be phagocytosed. Mutation of the RGD to RAD causes the protein to act as a dominant negative and inhibit phagocytosis of apoptotic cells.

MFG-E8 shares amino acid homology (48% identity) and protein structure with Del-1. MFG-E8 is a secreted glycoprotein with 2 EGF-like repeats followed by a proline-threonine-rich region and two discoidin-like domains; the major difference is the substitution of the proline-threonine-rich region for the third EGF-like repeat in MFG-E8. Both proteins have an RGD motif in the second EGF-like repeat which binds integrin $a_v b_3$. Furthermore, mutation of the RGD motif is capable of blocking the angiogenic or phagocytic activities of Del-1 and MFG-E8, respectively. One group has reported a similar role for phagocytosis of apoptotic cells for Del-1. Hanayama R, Tanaka M, Miwa K, Nagata S. Expression of developmental endothelial locus-1 in a subset of macrophages for engulfment of apoptotic cells. *J Immunol* 172(6) (2004) 3876-82.

As used herein, "biomaterial" means, without limitation, a material such as a matrix, hydrogel, polymer, tissue scaffold, bone graft, demineralized bone matrix, resorbable carrier materials including collagen sponges, or cellular support that includes a biologic agent. For purposes of the present invention, Del-1, whether as a protein or encoding gene, constitutes at least one of the biologic agents in biomaterials of the present invention.

In an adult, bone maintenance is a dynamic process including continuous cycles of breaking down and rebuilding of bone. Bone is broken down by osteoclasts and built up by osteoblasts. Bone is composed of outer cortical and inner trabecular bone, as well as cartilage, haemopoetic and connective tissues. The outer cortical bone makes up around 80% of total bone mass, and has a principal mechanical function. The inner trabecular bone is a spongy lattice of fine bone plates filled with haemopoetic marrow, fat containing marrow, and blood vessels. Bone is covered by a fibrous membrane called the periosteum, which is rich in capillaries for bone nourishment.

For purposes of the present invention, the term "cartilage" means a type of dense connective tissue composed of chondrocytes that are dispersed in a firm gel-like substance, called the matrix. Cartilage contains no blood vessels and nutrients must diffuse through the matrix. Cartilage is found in the joints, rib cage, ear, nose, throat and between intervertebral disks. Chondrocytes are the only cells found in cartilage and are responsible for producing and maintaining the matrix. From least to terminally differentiated, the chondrocytic lineage is: Colony-forming unit-fibroblast (CFU-F)→Mesenchymal stem cell/marrow stromal cell (MSC)→Chondrocyte→Hypertrophic chondrocyte.

The term "callus" or "callous" refers herein to fracture union tissue. Typically a callus is an unorganized meshwork of woven bone developed on the pattern of the original fibrin clot, which is formed following fracture of a bone and is normally ultimately replaced by hard adult bone, called also bony callous.

The term "anoikis" means apoptosis induced by inadequate or inappropriate cell-matrix interactions and is involved in a wide diversity of tissue-homeostatic, developmental and oncogenic processes. Apoptosis refers to a type of cell death in which the cell uses specialized cellular machinery to kill itself (therefore "programmed cell death"). Apoptosis is mediated in large part through the action of "caspases", which are defined circularly as any group of proteases that mediate apoptosis. The relationship between integrin-mediated cell adhesion signals and apoptosis is central to the anoikis process. Thus, in in vitro models, keratinocytes undergo apoptosis (anoikis) as a consequence of cell-detachment. Caspase 8 is known to be one of the first caspases activated in response to cell-detachment of keratinocytes. See Marconi A et al. *J Cell Sci* 117(Pt 24) (2004) 5815-23.

The present inventors first became interested in Del-1 as a factor that might be involved in wound healing. First experiments were designed to look at whether Del-1 might be regulated in wound healing. This was done with a simple mouse excisional wound model. Small areas of full thickness skin are excised and the wounds allowed to heal by secondary intention, which typically takes 12 days in normal animals. Wounds were harvested from mice at different times in wound healing and analyzed using immunohistochemistry. Antibodies to Del-1 were generated by one of the inventors and used in these experiments. The experiments demonstrated that Del-1 is not normally expressed in normal skin, but is up-regulated during wound healing. Del-1 protein was found to be detected in the wound be beginning at 3 days post-wounding with peak expression seen at 7 days post wounding. After complete wound healing, there was no longer any expression seen in the skin. The expression was seen in the granulation bed of the wound and correlated with when angiogenesis would be occurring.

These data gave impetus to investigate a potential use of Del-1 in wound healing. This was approached in two ways. First, a transgenic mouse was generated that had the Del-1 gene under the control of the keratin 14 promoter (K14-Del-1) for tissue restricted expression of Del-1 in the epidermis. Secondly, Del-1 protein was purified from a baculovirus vector system for direct application to wounds. Functional activity of this protein was confirmed using a CAM assay to demonstrate that the purified protein was capable of inducing angiogenesis at the protein concentrations previously described by Hidai et al. *Genes and Development* 12 (1998) 21-33.

A novel pathway and a new therapy have been uncovered by the present inventors from studies to determine whether Del-1 overexpression would ameliorate wound healing. Transgenic mice that were engineered to over-express Del-1 in the skin were shown to re-grow their hair considerably faster after it is removed by depilatory agents. In the model system employed Del-1 was constitutively expressed under the control of the keratin-14 (K14) promoter. Keratins 14 and 5 are structural components that characterize the basal keratinocytes of the epidermis and the outer root sheath of the hair follicle. The promoters of these genes control this tissue-specific distribution. Thus, by placing Del-1 behind the K14 promoter in transgenic mice, it was determined by the present inventors that expression of Del-1 in these tissues dramatically increases the rate of hair growth. Based on this finding, a modality for using Del-1 encoding genes or proteins to increase hair growth was derived.

In the K14-Del-1 system it was confirmed there was elevated expression of the protein in the epidermis using immunohistochemistry. However, comparing the same excisional wound in normal mice, no differences were seen in the rate of wound closure. Analysis of the skin for increased vascularity was also negative. Immunohistochemistry (IHC) was performed with CD34 and vWF antibodies, which did not detect increased vascularity. However, it was noticed that the hair on the Del-1 transgenic animals grew back faster over wound sites. Wounding is a stimulus for "anagenesis", the growth of new hair follicles. As model system that would focus specifically on hair re-growth, use of depilatory creams is a standard approach in the literature to initiate anagenesis. These creams chemically remove hair thereby stimulating new hair growth. Cutting or shaving the hair does not have this effect.

Normally, hair returns about 16 days after depilation. However, in the K14-Del-1 animals, hair re-growth by 12 days was detected. This was confirmed by histology. It is known that hair follicle regeneration requires a blood supply, and change in vascularity were considered with this model but were not detected.

The transgenic results were confirmed using normal mice where it was shown that the phenomena of Del-1 enhancement of hair growth was not an artifact of the transgenic system. Injection of purified protein was also able to increase the regrowth of hair from depilitated areas in normal, non-transgenic mice.

Mice were shaved over the back, while depilation was applied on only a discrete area. Del-1 protein was administered by intradermal injections of Del-1 protein or carrier on either flank of the animals. Hair regrowth also appeared to be enhanced based upon histology although not to the degree seen in the K14-Del-1 animals. This was attributed to that the transgenic animals had persistent levels of the protein all the time compared to periodic injections. This finding provides a novel function for this protein and represents an additional approach to current pharmaceutical methods of hair regeneration.

In one embodiment of the invention for the treatment of baldness, Del-1 protein is administered topically in a penetrating cream. Alternatively, a gene construct encoding Del-1 is administered to area where hair growth is desired. The construct can be administered as unformulated plasmid DNA or can be formulated in a transfection enhancing carrier as known to those of skill in the art. Examples of Del-1 gene expression constructs and formulations have been described, such as for example in WO02/061040. Alternatively, the Del-1 construct can be administered by gene gun or electroporation.

Because of the newly discovered phenotype, the present inventor examined the role of Del-1 in normal skin and hair development. Embryonic skin is a simple single layer epithelium until about Day 15 of embryogenesis. At this point, hair follicle formation and thickening of the skin becomes apparent. Hair follicles are formed prior to birth, but do continue to grow afterwards. The body hair is termed pelage hair follicles as distinguished from the whiskers on the snout that are termed vibrissae follicles. The vibrissae form a couple of days earlier than the pelage. To study this, a Del-1-LacZ knock-in transgenic model was developed. In this transgenic, the LacZ gene is inserted into the normal position of Del-1, and is controlled by the Del-1 promoter. This allows staining for LacZ to be used as a surrogate for Del-1 expression. When bred to homozygosity, the animals become functional null mutants.

In the developing embryo, no evidence was found of expression of Del-1 during pelage hair follicle formation. Del-1 was expressed in the mature vibrissae hair follicle. Interestingly, it is located in a region of the hair follicle that has been termed the bulge region. This region is thought to contain regional stem cells that subsequently are capable of becoming hair cells or epidermis.

An additional finding was noted while performing analysis of Del-1 expression in the vibrissae whiskers of the snout. Histologic sections through the snout revealed very high expression in the cartilage of the snout. It had previously been reported that Del-1 was present in hypertrophic cartilage (cartilage that is on the way to bone), and there was one report of Del-1 in articular cartilage. It had been assumed in the past that the expression of Del-1 in the hypertrophic cartilage was due to the vascular invasion that turned the cartilage into bone.

Using transgenic lines in which a marker gene is used as a surrogate for activity from the normal Del-1 transcriptional regulatory regions (also referred to herein as the "Del-1 promoter"), it was determined by the present inventors that, during embryogenesis, Del-1 is prominently and strikingly expressed in the developing vasculature, portions of the brain, and throughout the hypertrophic cartilage of the skeleton. It was further discovered that Del-1 is expressed in the mature skeleton, in every cartilaginous structure, including costal, tracheal, and articular cartilage. In addition, it was found in the cranial sutures of the skull.

Because of this high expression in the skeletal elements, knockout mice were reanalyzed to see if there were subtle defects in skeletal development that had not been previously noted. Despite a fairly exhaustive search in both young and old animals, such a defect was not found. Del-1 transgenic null mutants appear phenotypically normal. There are no vascular or skeletal anomalies, and post-natal development is also normal. The mice are fertile and age without apparent problems. Furthermore, no developmental anomalies in the bone are noted. However, it was found that these mice do demonstrate a different response from wild type littermates when they undergo bony fracture.

Initial experiments consisted of performing a small incision in the hindlimbs of 6 week old mice. The tibia was identified and cut directly with scissors. Fracture is confirmed by X-ray. If these fractures are unstabilized, they will heal through endochondral ossification. This consists of first developing a soft tissue callous at the fracture site followed by cartilage. The cartilage is hypertrophic cartilage that undergoes vascular invasion followed by replacement with mature bone.

Initially after fracturing, there is little apparent difference between wild type and knock-out animals. Differences became apparent at the third week where on plain x-ray, it starts to become apparent that there is less bone forming in Del-1 knock-out animals. Both Del-1 knock-out and wild-type littermates are capable of healing the fracture, but there seems to be less bone being formed in the knock-out animal. Micro computerized tomography (CT) was used to quantitate fracture healing. The CT is capable of defining the amount of bone callous and differentiating bony from non-bony callous. Using this technique, it was confirmed that there is less bony callous being formed in the knock-out animals.

Del-1 effects were also studied in an in vitro model of bone and cartilage differentiation. A population of adipose derived pluripotent cells was used under conditions under which these cells can be differentiated into fat, bone and cartilage. Bone differentiation was demonstrated with von Kassa and alkaline phosphatase staining. Cartilage differentiation was demonstrated with Alcian blue staining as well as by analysis of different markers of both bone and cartilage differentiation.

Using this system of differentiating cells, expression of Del-1 was investigated in differentiating bone and cartilage. Although significant up regulation of Del-1 during bone formation was not overt, there is a significant amount of Del-1 produced during cartilage differentiation. This confirms the value of Del-1 as a marker of cartilage growth.

Mechanistically, it is believed by the present inventors that Del-1 promotes the development of a larger cartilaginous scaffold during fracture healing due to its anti-apoptotic effect on chondrocytes ultimately leading to a larger volume of bone callus. Another potential mechanism is that Del-1 promotes vascular invasion, which is required for ossification to occur, through its anti-apoptotic effects on endothelial cells. Either or both mechanisms can be functioning to create this phenotype.

Based on the present discovery of Del-1 in bone morphogenesis and healing, the present inventors investigated the potential role of Del-1 in tissue engineering to provide enhanced rebuilding of replacement tissues. Primary chondrocytes grown on Del-1 coated plates increased cell numbers at a faster rate and had greater survival as measured by trypan blue exclusion. Thus, in one embodiment of the invention, it is anticipated that autologous chondrocytes are harvested from a patient in need of engineered tissues and are used to seed scaffolds in vivo or in vitro in the presence of Del-1 protein. Alternatively, a population of cells can be transfected with a Del-1 expressing gene construct, whereby expression of Del-1 by the transfected cells provides an ongoing local source of Del-1 protein.

The chondrocytes growing on a scaffold in vitro can be considered an explant culture of an ultimately desired implant, be it for engineering of tissues for the cartilaginous outer structure of the nose, nasal septum, pinae of the ear, articular cartilage, tracheal implants, penile implants, bone defect filler, etc. The Del-1 provides enhanced survival and proliferation of the chondrocytes thus providing for a more rapid preparation of the implant for ultimate surgical implantation. Titering of the most advantageous concentration of Del-1, alone or in conjunction with other growth factors, can be readily determined by microscopic observation of the explant cultures although further measures of viability may be optionally employed.

A number of different scaffold materials are available to those of skill in the art and other suitable scaffolds are likely to be developed in the future. Presently available scaffold materials include, without limitation, elastin-like polypeptides, chitosan, hydroxybutyl chitosan, poly-lactic acids [including poly L lactic acid (PLA) and poly-d,l-lactic acid (P(D,L)LA)], polyglycolic acid (PGA, such as that available for instance from Albany International Research Co. "AIRESCO"), poly DL Lactic-co-glycolic acid (PLGA), collagen and collagen based materials including collagen-hydroxyapatite [Col-HA], collagen-silk, collagen-glycosaminoglycan, collagen-elastin-glycosaminoglycan, cross-linked type I and type II collagen matrices with and without attached chondroitin sulfate, alginate and agarose hydrogels, hyaluronic acid polymers including glycidyl methyacrylate-HA (GMHA) conjugates, porous gelatin scaffolds (such as Surgifoam®), gelatin/chondoitin-6-sulfate/hyaluronan tri-copolymers, electrospun collagen and elastin, photocrosslinkable hyaluronan (HA-MA), fibroin-hydrogel sponges, poly (e-caprolactone), beta-tricalcium phosphate (beta-TCP), mineralized and partially or fully demineralized biomaterials derived from bovine bone matrix, etc.

Alternatively, wholly synthetic materials such as polyurethane, polyester-urethane polymer (DegraPol®), divinyl, tetrafunctional poly(ethylene glycol) (PEG), polyvinyl alcohol (PVA), trimethylene carbonate (TMC), etc., are potentially available.

In one embodiment, demineralized bone matrix (DBM) is used by mixture together with Del-1 proteins, Del-1 encoding vectors, or Del-1 transfected autologous cells for treatment of fractures, spinal fusions, filling of bone defects, and in conjunction with bone grafting. A number of DBM products are presently commercially available, such as for example, DYNAGRAFT brand DBM (GenSci: 49-64% DBM with a Pluronic copolymer), GRAFTON brand DBM (Osteotech: 31% DBM with glycerol), DBX brand DBM (MTF: 74-93% DBM with hyaluronic acid), OSTEOFIL brand DBM (RTI: 49% DBM with collagen), ALLOMATRIX brand DBM (Wright: 86% DBM with calcium sulfate). (Parikh S N, *Journal of Postgraduate Medicine* 48 (2002) 142).

Different scaffolds support the growth of different cell types in different environments under the influence of different growth factors. Although seemly complex, determination of the best scaffold for growth and population by a particular cell type in the presence of Del-1 is readily determinable empirically in accordance with procedures known to those of skill in the art. For one of many examples of testing the effects of different scaffold materials for a particular growth factor, see Xu et al. "Evaluation of different scaffolds for BMP-2 genetic orthopedic tissue engineering." *J Biomed Mater Res B Appl Biomater.* Jul. 15, 2005; [Epub ahead of print].

In one embodiment of the invention, Del-1 protein or a Del-1 encoding gene expression construct is administered together with scaffolding materials, prosthetics, carrier matrices or DBM to promote the early recruitment, growth and differentiation of chondrocytes at the site of the implant.

Del-1 encoding gene expression constructs can be administered as unformulated Del-1 encoding nucleic acids or can be formulated in a transfection enhancing carrier as known to those of skill in the art.

In one embodiment of the invention, Del-1 protein or gene expression construct is mixed with a polymer gel for injection into and treatment of torn cartilage. One such polymer gel that may be optionally employed is a liquid polymer that solidifies when exposed to heat. See e.g. Betre H. et al. *Biomacromolecules.* 3(5) (2002) 910-6. Thus, the polymer containing Del-1 protein or gene can be injected or poured into torn cartilage tissue for adaptation to contours of the tear. The material is then cured to a solid where it serves as a scaffold for the patient's chondrocytes to migrate and proliferate to rebuild the cartilage. In an alternative embodiment, the patient's own cartilage cells are grown in the laboratory under the influence of at least Del-1 and then mixed with the pre-cured scaffold for implantation into the tear in the patient's joint. Further Del-1, without or without additional growth factors can be added to the scaffold as it is formed or if desired at the time of implantation.

An alternative to using autologous chondrocytes is to utilize a population of autologous multi- or pluripotential cells that can be expanded into the tissue of choice. Ideally, tissue engineered cartilage can be derived from a readily available autologous source, can be expanded in a short amount of time, and can be used to make sizeable constructs capable of resurfacing entire joint surfaces. One potential source of multipotent cells that has been studied is adipose derived mesenchymal cells (AdMSCs). These cells can be derived from fat and differentiated into muscle, cartilage, bone and nerve. They can be harvested in large numbers and are also capable of expansion to significant numbers. Fat can be harvested in a much less invasive procedure than required to harvest a specimen of articular cartilage. The current strategy used by Genzyme (Carticel) to expand chondrocytes is slow because of the poor ability of chondrocytes to expand in vitro. AdMSCs have a much greater proliferative rate and can reach the desired cell mass in a shorter time. For the same reason, AdMSCs can be used to make cartilaginous constructs that are large enough to cover the entire surface area of the desired tissue.

Other sources of autologous multipotent cells have been examined including those derived from bone marrow, synovium, periosteum, and skeletal muscle. The ability to differentiate into cartilage and bone is present in these other populations of multipotent cells, and Del-1 would have applicability in all of these systems.

In another, embodiment of the invention, Del-1 protein or a Del-1 encoding gene expression construct, is impregnated in a absorbable collagen sponge and implanted adjacent to transferred autologous bone during bone grafting procedures, including reconstructive maxillo-facial surgery, spinal fusion, cranial bone defects, open fracture repair, fracture.

In another embodiment of the invention, Del-1 protein or a Del-1 encoding gene expression construct, is introduced together with one or more additional growth factors, or gene constructs encoding the growth factors, including transforming growth factor (TGF-β), bone morphogenic proteins (BMPs), fibroblast growth factors (FGFs), insulin-like growth factors (IGFs), platelet-derived growth factors (PDGFs), and vascular endothelial growth factors (VEGFs).

For purposes of Del-1 gene expression, the Del-1 encoding nucleic acid can be any suitable type able to drive expression of Del-1 within cells associated with a desired region for expression. Thus, the nucleic acid can be RNA, cDNA, genomic DNA, etc. Most typically, the nucleic acid includes a cDNA-like coding region within an expression construct (a.k.a. gene expression construct) that includes further 5' and 3' elements necessary for transcription and translation and thus expression of Del-1 protein. By "cDNA-like" it is meant a coding region that is more compact that that of the genomic DNA in that most intronic regions are removed. However, one or more introns may be retained for purposes of increased expression or one or more heterologous introns may be added. The expression construct is likely to have a promoter able to drive the expression of the coding sequence within the desired cells as well as a polyadenylation sequence following the coding sequence. Many promoters and polyadenylation sequences are known to those of skill in the art as suitable for such use.

Many different types of vectors are known in the art and are available for carrying and propagating the expression construct including plasmids, cosmids, yeast artificial chromosomes (YACs), viral vectors, etc. Methods for engineering vectors to include expression constructs are well known in the art. For purposes of the present invention, it is understood that the Del-1 protein is encoded by a nucleic acid, is expressed in and under the control of an expression construct that includes 5' and 3' elements necessary for engaging the transcription and message processing apparatus of the eukaryotic cell, and is propagated by a vector. To the extent that these terms may be used interchangeability, this is not in a limiting context as would be well understood by one of ordinary skill in the molecular biological arts. Examples of Del-1 gene expression constructs and formulations have been described, such as for example in WO02/061040.

For purposes of the present invention, Del-1 is used to enhance the growth, differentiation and/or survival of chrondrocytes, bone healing and hair re-growth. For this purpose, Del-1 is introduced into a local vicinity where such processed are desired. Del-1 can be introduced as a protein or as a Del-1 encoding and expressing nucleic acid for transfection of at least one cell associated the local vicinity. For bone healing and growth, the relevant vicinity includes the bone itself as well as immediately adjoining areas within or surrounding the bone, including bone marrow, periosteum, muscle, fascia, tendons, ligaments, and endothelial cells. Cells generally found within bony structures include bone marrow stem cells, preosteocytes, osteocytes, chondrocytes and stromal cells. Cells in surrounding tissues include periosteal or fascial cells and muscle cells. Alternatively, the cells can be from exogenous tissues, such as tissue grafts.

The following examples are included for the sake of completeness of disclosure and to illustrate the methods of making the compositions and composites of the present invention as well as to present certain characteristics of the compositions. In no way are these examples intended to limit the scope or teaching of this disclosure.

Example 1

Expression of Del-1 in Acute Wound Microenvironment Model In Vitro

Figure 1:
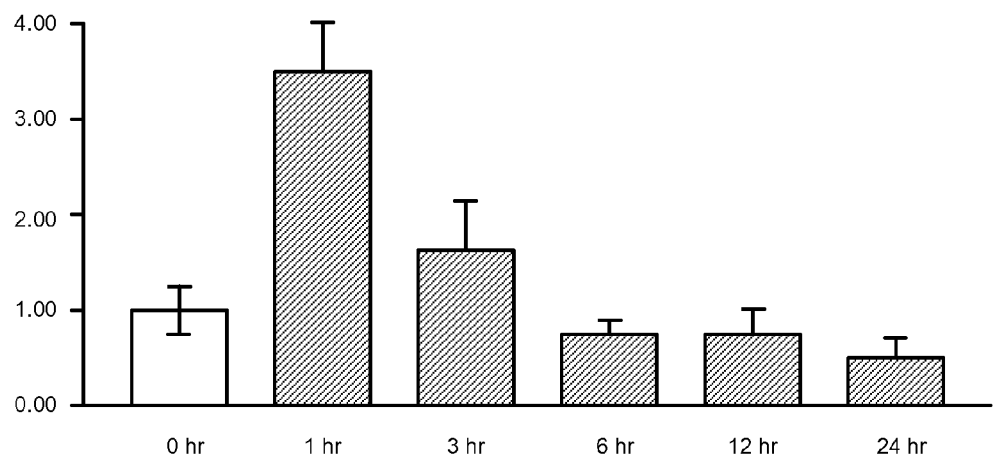

It has been reported that the acute wound environment can be modeled in vitro through modulation of serum levels. Murine 3T3 cells in cell culture were quiesced and then serum-stimulated according to a model of acute wound microenvironment essentially as described by Iyer V R et al. *Science* 283 (1999) 83-7. Total RNA was harvested, reverse transcribed to cDNA and analyzed by real-time qPCR at 0, 1, 3, 6, 12 and 24 hours post stimulation. In this model and as depicted in FIG. 1, it was found that Del-1 RNA rapidly peaked at 1 hour (3.5±0.5×baseline) and returned to baseline equally rapidly, remaining there for the duration of the 24 hour time course.

Example 2

Expression of Del-1 in Acute Wound Healing Model In Vivo

Dorsal excisional wounds of 4 mm$^2$ were induced on the back of adult mice. Wound tissue was harvested at 0, 1, 3, 5, 7, 11 & 14 days. Del-1 IHC was performed using standard methodology. In brief, paraffin sections were reacted with an antibody directed to Del-1 followed by a secondary goat anti-rabbit antibody conjugated to alkaline phosphatase. Staining was performed using a chromogenic substrate for alkaline phosphatase and the slides were counter-stained with hematoxylin. No detectable Del-1 was found in unwounded skin. By 3 days post-wounding (dpw), very small amounts of Del-1 were detected in wound edges and in the granulation bed. By 7 dpw, significant amounts of Del-1 were detected in the wound bed and at the edges. The identity of the expressing cells was unclear, but appeared to be most prominent in fibroblasts in the wound bed. By 14 dpw, the wound healed with no detectable Del-1. Protein expression of Del-1 during wound healing was shown to have a temporal and spatial profile highly correlated with the time at which peak angiogenesis in wound healing takes place.

Example 3

Del-1 Expression in Development Based on Marker Transgenic Lines

The expression of Del-1 during murine development was followed using transgenic mice that had the LacZ gene "knocked-in" to the native gene. Heterozygous animals stain blue in sites where Del-1 is transcriptionally active, and homozygote animals are null mutants. By cloning marker genes behind an untranslated regulatory region of the Del-1 gene, expression of a marker gene can be used to reveal normal transcriptional activity of Del-1 during development. In order to study the temporal and spatial expression of Del-1 during development, the original mouse line that was used to identify Del-1 was employed. This transgenic mouse has a LacZ gene inserted into the normal coding region and is driven by the native promoter of Del-1. Heterozygote animals are phenotypically normal and will stain for LacZ where Del-1 is being expressed. Homozygote animals are functional knock-out animals. (Hidai, et al. *Genes and Development.* 1998. 12(1):21-33). Transgenic mice were generated in accordance with standard methodology, generally in accordance with the system described in Boutet, Quertermous and Fadel, *Biochem J* 360 (2001) 23-29 and Sinha et al *Molecular and Cellular Biology* 20 (2000) 2543.

Figure 2:
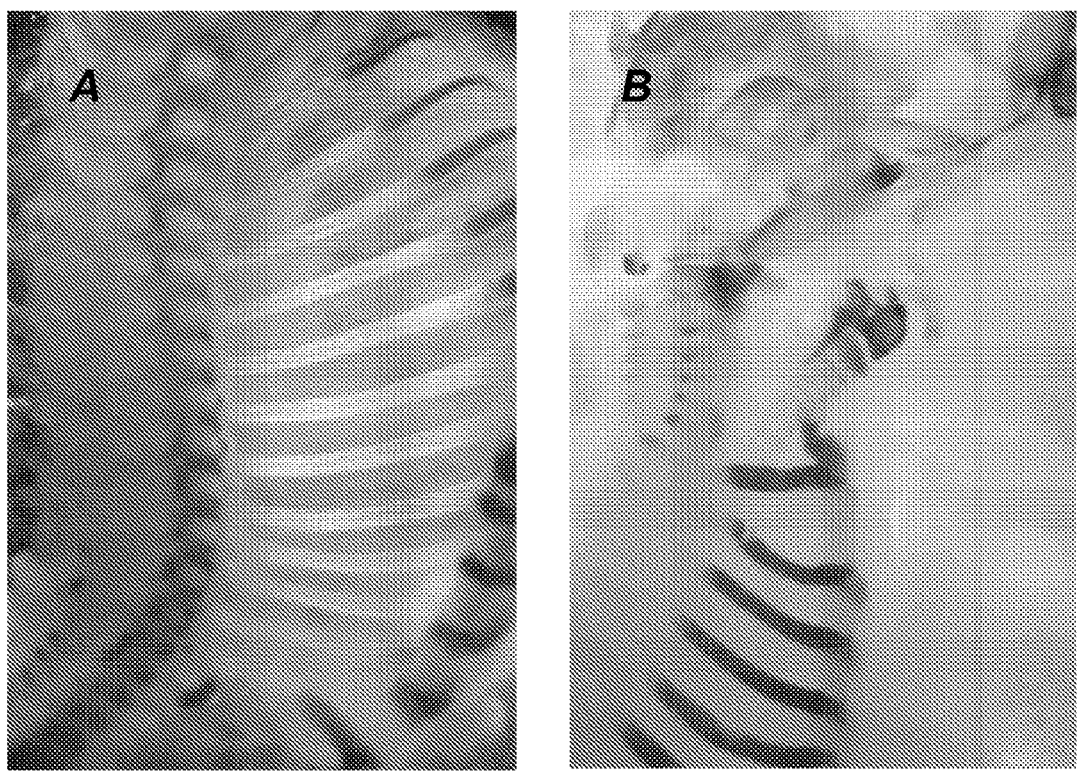

Sites of Del-1 expression were confirmed using whole mounts and histological sections. During embryogenesis in the Del-1 marker transgenic mice, Del-1 was prominently transcriptionally active in the developing vasculature, portions of the brain, and in cartilaginous structures. Transcriptional activity of Del-1 was found in hypertrophic cartilage as well as mature cartilage. Del-1 transcriptional activation was detected early during skeletogenesis as the cartilaginous skeleton developed. See FIG. 2. During skeletal ossification, Del-1 expression was lost in bone, but persisted in cartilaginous structure including the articular, tracheal, and costal cartilages. This expression persisted into the adult animal.

Figure 3A:
Figure 3B:
Figure 4A:
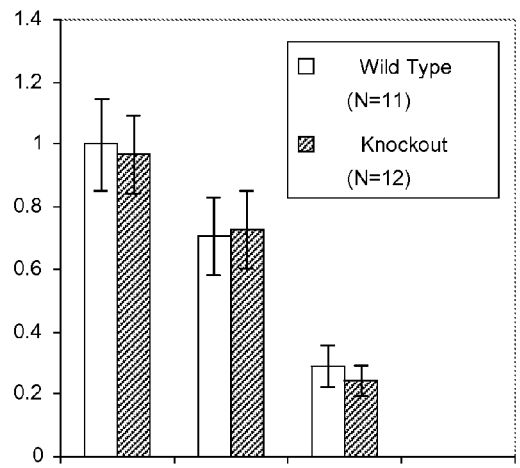
Figure 4B:
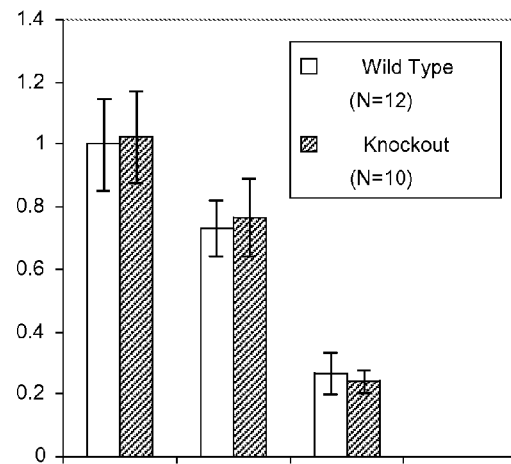
Figure 4C:
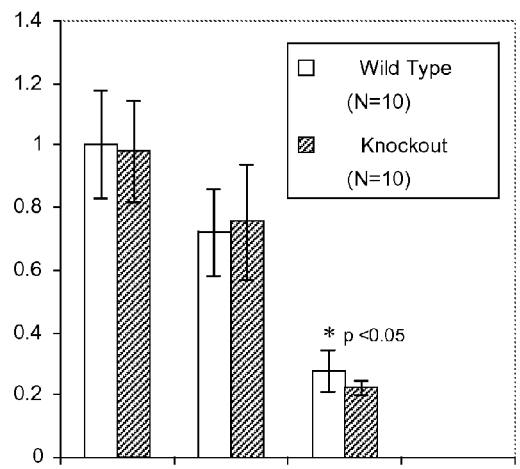
Figure 4D:
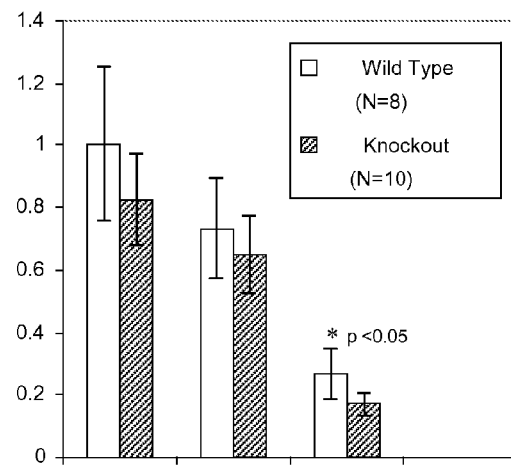

Interestingly, the Del-1 regulatory region was not only found to be highly active in cartilage as depicted by blue LacZ staining and was also found to have a unique expression pattern in the facial whisker (vibrissae) follicles as depicted in FIG. 3A with the wild type stained in FIG. 3B.

Example 4

Del-1 Involvement in the Healing of Bony Fractures

A Del-1 knock-out transgenic line was developed in which expression of Del-1 is abolished. The knock-out mice were generated by now standard technology generally in accordance with the system described in Hogan B, et al. *Manipulating the Mouse Embryo: A Laboratory Manual.* Plainview, N.Y.: Cold Spring Harbor Laboratory Press (1994), as referenced in Ishida, Choi, Kundu, Hirata, Rubin, Cooper and Quertermous, *J Clin Invest* 111 (2003) 347-355. The system employs transgenic "knock-out" (KO) mice that contain germline insertional loss-of-function mutations through the use of pluripotent mouse embryonic stem (ES) cells that are combined with non-transgenic mouse blastocysts to produce a chimeric embryo. Differences in the coat color of ES donor mice and blastocysts host mice are used to identify transgenic founder animals. The offspring have a mosaic coat color reflecting their chimeric genotype. Transgenic founder lines are identified as agouti offspring that arise from crossing chimeric and albino mice.

Del-1 knock-out or null mutants are born and develop with phenotypically normal appearance. There are no vascular or skeletal anomalies were detected during the lifespan of null mutants using dissection and radiology. The mice are fertile and age without apparent problems. However, these mice do demonstrate a different response from wild type littermates when they undergo bony fracture.

For in vivo investigations, unstable tibial fractures were made on six week old wild-type and Del-1 knock-out mice. These fractures are unfixed and the animals will heal these through the process of endochondral ossification. Weekly X-rays were examined for five weeks, and then the tibias were harvested and stained. In addition the callous volumes were analyzed by micro CT with 3D reconstruction. This assay measures bone by its mineralization.

Initially, there is no difference between knockout and wild type during the first few weeks following fracture. Following fracture by 4 weeks, tibial fractures of Del-1 knock-out mice had smaller fracture callouses at the fracture site by X-ray and gross examination. Micro CT with 3D reconstruction confirmed significantly less bony callous in the null mutants. FIGS. 4A-D depict the callous volume of Del-1 knock-out versus normal littermates following tibial fracture.

Heterozygote LacZ knock-in animals were used to examine Del-1 expression in fracture healing. Normal, uninjured bone does not have any significant Del-1 expression. However, 3 days after fracture, some expression of Del-1 is seen and this peaks at 14 days after fracture. This is coincident with the formation of hypertrophic cartilage at the fracture site.

Since endochondral bone heals through a process requiring a cartilaginous intermediate, the phenotype may be due to increased apoptosis of cartilage in the healing fracture. This function of Del-1 is not necessary as the fracture still heals. In summary, it appeared that Del-1 is expressed in developing and mature cartilaginous structures. No skeletal defects are noted during development or after maturity in knockout animals. Fractures heal in the same time frame in wild type and knock-out animals. Decreased callous formation is seen following fracture healing in Del-1 knock-out mice. Thus, although Del-1 is not expressed in normal bone, but is up regulated during normal fracture healing. As noted, bone healing goes through a cartilaginous intermediate, which forms the scaffold for subsequent mineralization to bone. The results indicate that the lack of the anti-apoptotic factor Del-1 in the cartilaginous intermediate of the knock-out animals leads to a smaller bony callus.

Example 5

In vitro MicroArray analysis of Gene Expression Following Del-1 Transfection

In order to identify a molecular mechanism for the phenotype of Del-1 expression during healing, DNA microarray experiments were performed of endothelial cells with and without Del-1. Genes whose expression was modified by Del-1 were analyzed and it was noted that Del-1 down regulated a number of genes involved in apoptosis.

NIH 3T3 cells were transiently transfected with Del-1 overexpression vectors as well as vector controls (all in quadruplicate). Overexpression by several hundred fold of Del-1 was confirmed using qRTPCR. Forty-eight hours after transfection, RNA was purified and Fluorochrome-labeled cDNA probes were made with these RNAs and used to perform microarray hybridizations in accordance with standard methodology. Briefly, probes were hybridized to Stanford microarray chips containing 43,000 individual gene fragments and analyzed with a GenePix scanner. Data was analyzed using GenePix Pro software and imported to the Stanford Microarray Database for further analysis. The following genes were found to be up- and down-regulated by Del-1.

TABLE 1

| Genes UP-REGULATED by Del-1 | |
|---|---|
| Jak2 | tyrosine kinase, activates STAT, mediates PDGFR |
| ELK1 | transcription factor involved in serum stimulation |
| Klf4 | zinc finger transcription factor involved in skin differentiation |
| Dss1 | interacts with BRCA2, involved in limb development |
| kRas2 | member of Ras family, involved in signal transduction |
| Slug | transcriptional repressor, involved in neural crest migration |
| Cyclin A2 | necessary for cell cycle progression |
| Lef-1 | transcription factor necessary for hair follicle formation |
| Genes DOWN REGULATED by Del-1 | |
| PDGFR-B | subunit of PDGF receptor; tyrosine kinase |
| Stat-1 | mediates transcription response to interferon |
| NFYB | transcriptional activator of collagen I |
| Abl1 | tyrosine kinase: cell prolif, cell diff, & stress response |
| Wnt3A | ligand for frizzled: cell-cell signaling, neural tube development |
| N-myc | transcription factor involved in oncogenesis |
| MAP4K4 | serine/threonine kinase involved in TNF signaling |
| Xbp1 | X-box transcription factor necessary for hepatocyte growth |
| FGFR1 | receptor for FGF |

Example 6

The Role of Del-1 in Apoptosis

Microarray analysis of the genomic response to Del-1 treatment confirmed down regulation of a number of apoptosis-related genes including caspase 8. HUVECs were grown with or without the presence of Del-1 and the mRNA harvested for microarray analysis as described above. This demonstrated the down regulation of a number of genes involved in apoptosis including numerous caspase genes. Based on the microarray results showing that Del-1 downregulates some genes thought to be involved in apoptosis, experiments were conducted to directly address this question.

Figure 5:
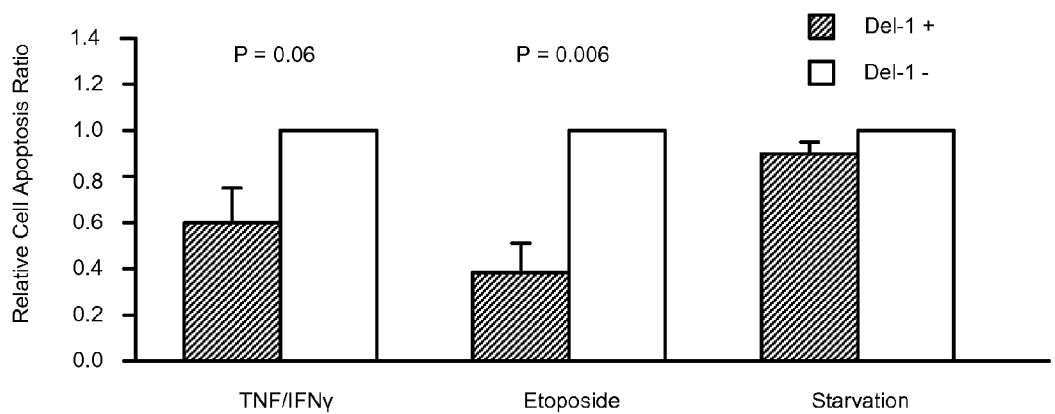
FIG. 5 depicts the effect of Del-1 on TNF/IFNγ and Etoposide Induced Apoptosis.

To correlate the microarray data with the biology, the ability of Del-1 to affect apoptosis was tested directly. HUVECs will undergo apoptosis when treated with TNF or etoposide, or with serum starvation. HUVECs were cultured on plates coated with or without Del-1, and treated with apoptotic stimuli. As depicted in FIG. 5, Del-1 protected endothelial cells from apoptosis due to TNF-α and etoposide, but not starvation. These experiments were repeated in primary osteoblasts and chondrocytes. There is no effect of Del-1 on osteoblasts, but chondrocytes are also protected from apoptotic stimuli.

In repeated experiments, HUVECs were plated on cell culture dishes coated with Del-1 or BSA as a control. Apoptosis was induced using TNF-α/IFN-γ (10 ng/ml), etoposide (100 μM) and serum starvation to activate both intrinsic and extrinsic pathways of apoptosis. It was found that there was a significant decrease in the numbers of apoptotic cells following activation of either the intrinsic or extrinsic apoptotic pathways when HUVECs were grown on Del-1. Analysis of cell death was done by trypan blue exclusion or WST-8 assay. The presence of apoptosis confirmed by ssDNA ELISA assay and TUNEL assay.

Figure 6:
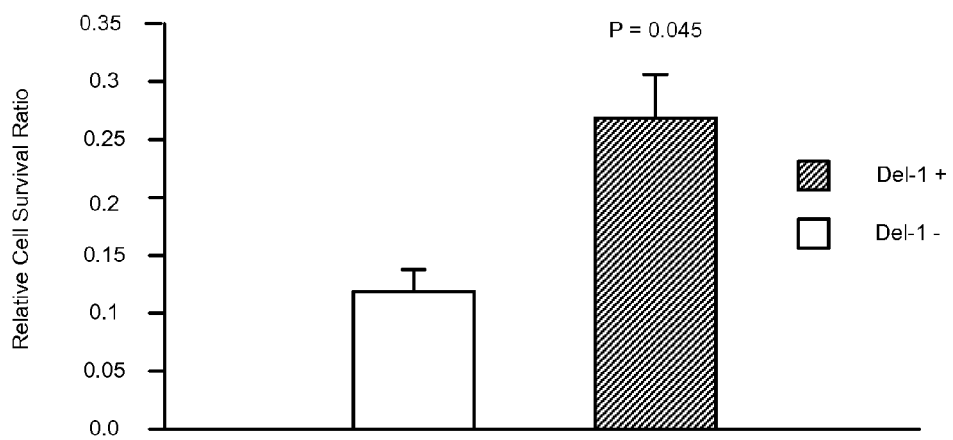
FIG. 6 depicts the effect of Del-1 on HUVEC anoikis.

Anoikis is a particular type of programmed cell death that is associated with loss of attachment. Normally, HUVECs require cell attachment or they will undergo anoikis. HUVECs are detached and cultured in suspension with or without Del-1. As depicted in FIG. 6, addition of Del-1 to the culture media was associated with significant protection of endothelial cells from anoiksis.

Example 7

The Role of Del-1 in Promoting Growth and Survival of Osteoblast

Del-1 is expressed in endothelial cells and cartilaginous tissue. The unique expression pattern in cartilage led the present inventors to investigate the role of Del-1 in skeletal development and repair. For in vitro studies, three-day-old mouse calvarial (from the skull) osteoblasts and three-week-old adipose-derived mesenchymal stromal cells (ADMSCs) were harvested. The two cell populations were treated with different doses of the Del-1 protein, and cells were counted to assess growth. These cell populations were also treated with osteogenic media to promote bony differentiation and treated with differing doses of Del-1. Differentiating the multipotent ADMSCs represents an in vitro model for osteogenic and chondrocytic development. For differentiation into osteoblasts, ascorbic acid, retinoic acid and BMP-4 are important to get terminal differentiation. To assess differentiation to bone, cells were analyzed for multiple markers of osteoblast differentiation including RNA expression of osteopontin, osteocalcin and Runx2, alkaline phosphatase enzymatic activity, and mineralization using von Kossa staining. RNA expression was detected using quantitative real time PCR (qPCR), alkaline phosphatase activity was quantified by harvesting cells and adding a chromogenic substrate, and mineralization detected with standard von Kossa staining.

It was found that no significant expression of Del-1 was seen during osteoblast differentiation. As the following example shows, Del-1 was also found to have the ability to decrease apoptosis in primary cultured endothelial cells and chondrocytes. During fracture healing, there is first a cartilaginous intermediate. This is subsequently invaded by blood vessels and undergoes ossification to create the fracture callus. Del-1 was shown to be important to early healing involving endothelial cells and chondrocytes.

Example 8

Del-1 in Tissue Engineering Using Chondrocytes

Figure 7:
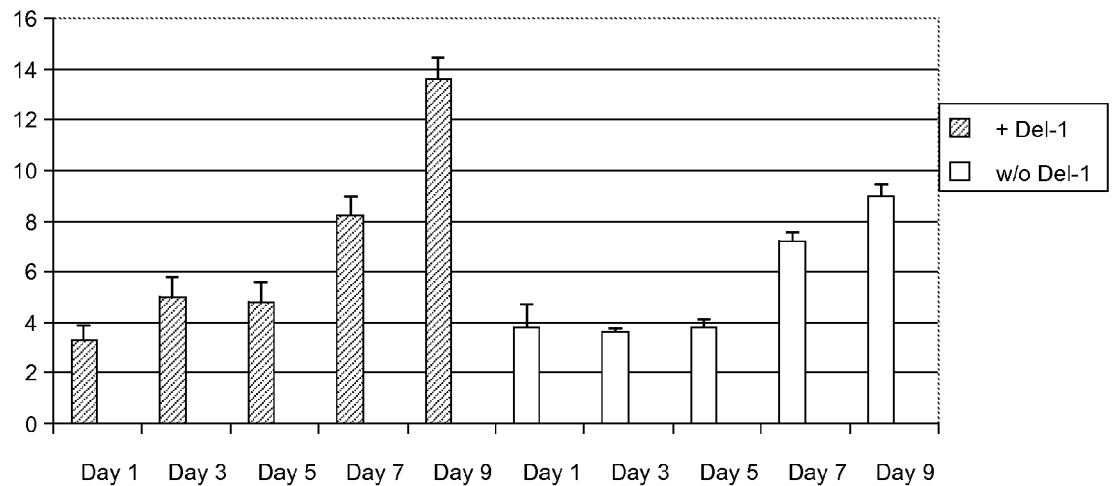
FIG. 7 depicts a time course of chondrocyte growth in vitro in the presence of Del-1.
Figure 8:
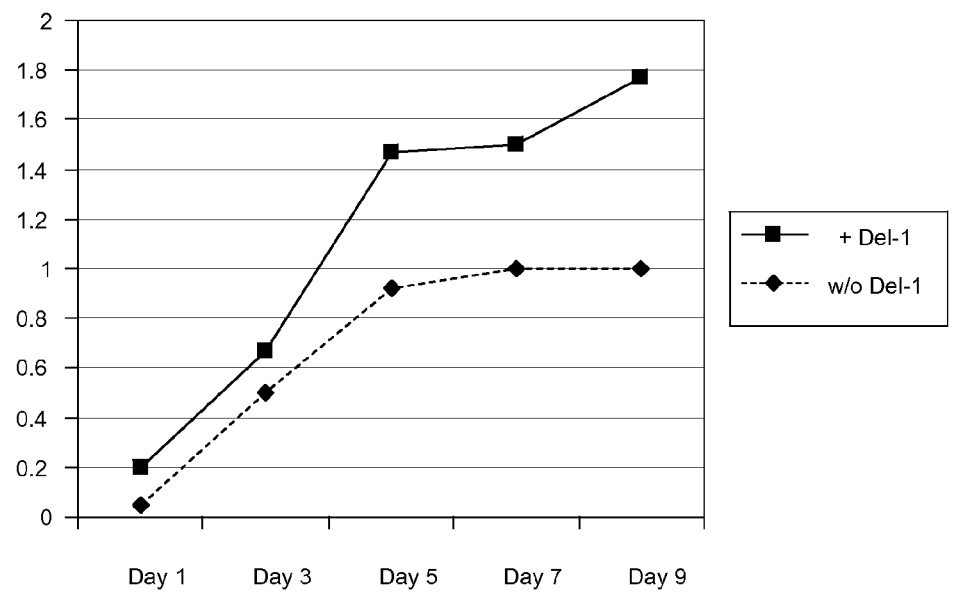
FIG. 8 depicts a time course of chondrocyte survival in vitro in the presence of Del-1.

To test the ability of chondrocytes to be protected from apoptosis, plates were coated with or without Del-1 protein at 100 micrograms/ml and dried. Primary chondrocytes were then added and cultured in normal chondrocyte growth medium obtained from Cambrex (Clonetics® Medium Systems). The Cambrex Chondrocyte Growth Medium contains R3-IGF-1, bFGF, transferin, insulin and FBS supplemented to the Cambrex Chondrocyte Basal Medium (which contains no growth factors). Cell number was assayed over several days. Although chrondrocytes are able to survive somewhat in this medium, in general chrondrocytes are difficult to grow and thus it is difficult to populate scaffolds ex vivo with autologous chondrocytes. As is apparent from FIG. 7, Del-1 is able to greatly enhance the growth of chondrocytes in culture. This is substantiated by the results of viability staining using trypan blue exclusion. Chondrocytes were grown as above and stained with trypan blue. Live cells that excluded the dye were counted showing increased numbers of live cells with the presence of Del-1 as depicted in FIG. 8. It is apparent that Del-1 potentiated the survival as well as the growth of chondrocytes.

Example 9

Del-1 in Tissue Engineering Using Stem Cells

In a separate line of investigation, the differentiation of multi-potent mesenchymal cells from adipose tissue (AdMSCs) into bone and cartilage was investigated as a possible cell source for tissue engineering. AdMSCs are harvested from the inguinal fat pads of mice and expanded in tissue culture. The addition of defined medium stimulates these cells to undergo differentiation into chondrocytes (Cambrex Chondrocyte Differentiation Medium) or osteoblasts (Cambrex Osteoblast Differentiation Medium). As compared with Chondrocyte Growth Medium, Chondrocyte Differentiation Medium contains TGF-β1 and lacks bFGF. As compared with Osteoblast Growth Medium, Osteoblast Differentiation Medium contains hydrocortosome-21-hemisuccinate and beta-glycerophosphate.

Cartilaginous differentiation was assessed by RNA expression of sox9 and collagen II, and alcian blue staining. During the differentiation of AdMSCs into cartilage, Del-1 was found to be one of the earliest genes up regulated by the cells implying that it is an early marker of cartilaginous differentiation. Furthermore, it implies that the mechanism of action of Del-1 is early during this process. Thus, Del-1 was found to be an early marker of chondrocytic differentiation.

Example 10

Del-1 and Hair Growth

Transgenic mice constitutively expressing the Del-1 gene constitutively in basal keratinocytes were generated in which the Del-1 coding region was cloned behind a keratin 14 promoter (K14-Del-1). The K14 promoter drives constitutive expression in the basal keratinocytes and was used to generate two separate transgenic mouse lines.

The Del-1 coding region was cloned behind the K14 promoter in accordance with standard methodology and as generally described in Sinha and Fuchs, *PNAS* 98 (2001) 2455. In the transgenic model chosen, insertion of the transgene can be readily detected as insertion of the transgene results ultimately in expression of a brown color in white "wild-type mice" generally in accordance with the system described in Hogan B, et al. *Manipulating the Mouse Embryo: A Laboratory Manual*. Plainview, N.Y.: Cold Spring Harbor Laboratory Press; 1994 as referenced in Ishida, Choi, Kundu, Hirata, Rubin, Cooper and Quertermous, *J Clin Invest* 111 (2003) 347-355.

When examined for wound healing, no significant difference detected between the transgenic mice and the wild-type in terms of wound healing at 2 wks post-wounding (i.e. the two groups had the same rate of re-epithelialization). However, a striking phenotype was discovered at 3 weeks post wounding. Stimulation of hair re-growth in areas of wounding that was significantly accelerated was observed in the Del-1 mice as compared to the wild-type mice. Six to eight week-old transgenic animals were shaved and depilated with NAIR® along the posterior midline. Wild-type littermates were used as controls, and tissues were harvested at 10, 12, 14, 16, and 19 days post-depilation. Progress of hair regrowth was followed by photography, histology, and IHC K14-Del-1 animals appear normal and heal excisional wounds normally. IHC confirmed increased Del-1 expression, but indicated no increase in vascularity. Following depilation, hair re-growth is grossly visible by day 15 in littermates compared to day 18 for normals. Full-length hair follicles were visible by histology at post-depilation day 15 in K14-Del-1 animals, while wild-type animals showed very rudimentary hair-follicle regeneration confirming this histologically. At 3 weeks post-wounding, dramatic re-growth of hair in the wounding areas was noted in the Del-1 transgenic mice.

Figure 9A:
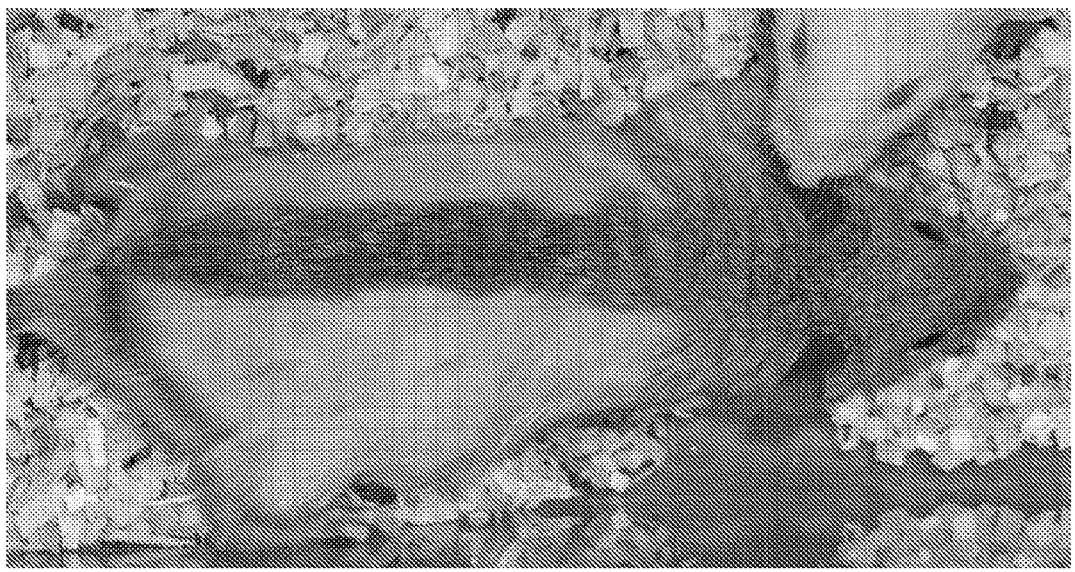
FIG. 9A is a photograph of a transgenic mouse that constitutively expresses Del-1 at 26 days post depilation in a strip down the center of the back.
Figure 9B:
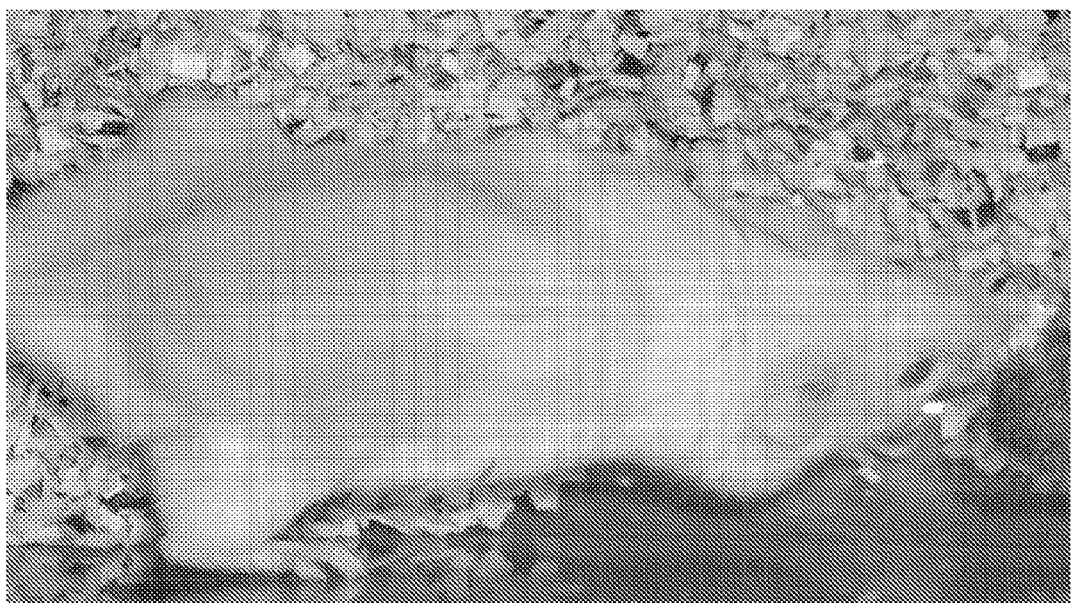
FIG. 9B is the wild type litter mate control after the same treatment.

Following the above observation, the effect of the depilation treatment was tested by shaving the entire back of Del-1 transgenic mice while applying NAIR® in a narrow strip down the center of the back. This controls for the effect on a single mouse. This treatment did not affect the rate of regrowth in the wide type mice but the depilation dramatically stimulated hair regrowth in the Del-1 mice by day 19 post treatment. As shown on FIG. 9A, by day 26 post-treatment, hair was completely regrown on the Del-1 transgenic mice in contrast to little regrowth for the normal littermates depicted in FIG. 9B.

Figure 10:
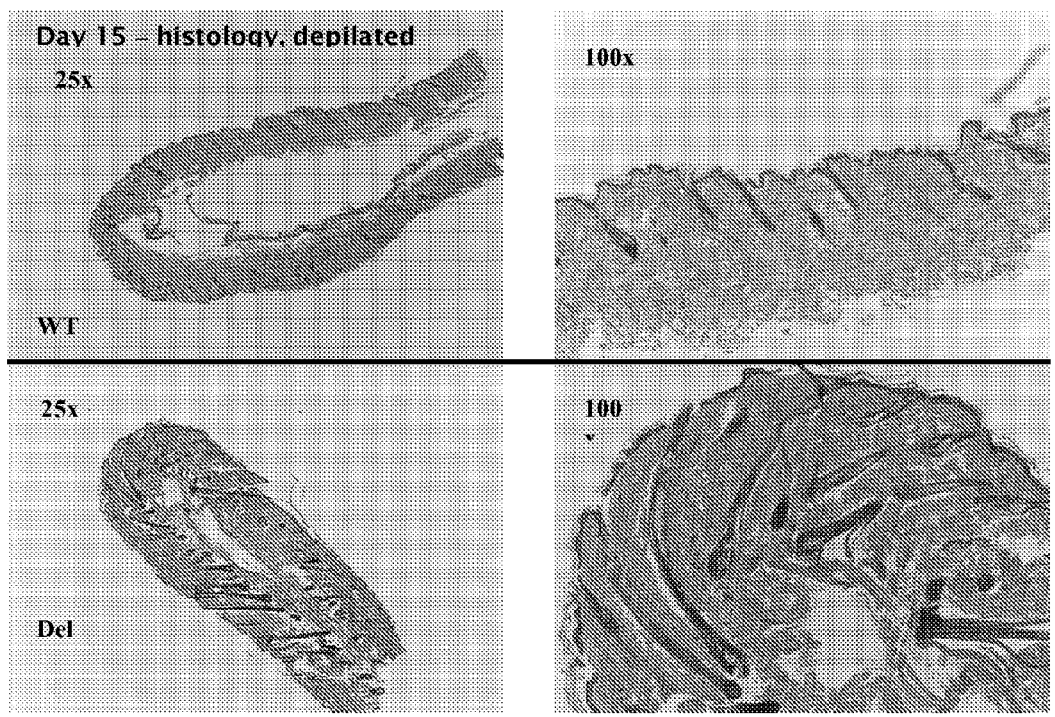
FIG. 10 represents the 15 day histology of depilated areas at 25× and 100× magnifications. The top two panels are from wild-type mice while the bottom two panels are from a transgenic mouse that constitutively expresses Del-1.

To study the mechanism of the Del-1 effect, histology was performed comparing the shaved areas with the depilated areas at day 15. As can be seen in the bottom two panels of FIG. 10, the growth of new hairs was dramatically accelerated in the Del-1 mice as compared with wild-type mice depicted in the top two panels of FIG. 10.

In order to confirm that the effect was due to Del-1 expression, wild type mice were shaved and then depilated in a band in a partial area of the shaved region. Purified recombinant human Del-1 protein was injected intradermally. Visually, Del-1 resulted in accelerated hair growth even where injected as a purified protein.

Confirming the effect histologically, the Del-1 protein injections dramatically increased the maturation of regrowing hairs as shown in the bottom panels of FIG. 11 as compared with the control injections in the top two panels of FIG. 11. It was concluded that constitutive expression of Del-1 in skin does not appear to increase vascularity or improve wound healing. Surprisingly however, it was found that Del-1 exposure led to increased hair growth following depilation.

Depilation is a known inducer of hair anagenesis and Del-1 appears to dramatically accelerate this process.

Example 11

Mechanisms of anti-apoptotic effect of Del-1

Efforts were undertaken to determine the role of the Del-1 RGD motif in its anti-apoptotic effect in endothelial cells. Integrin binding proteins are known to prevent apoptosis, and the RGD motif is the primary site of binding interaction. Del-1 has a number of potential signaling motifs including an RGD sequence but the role of the RGD sequence in mediating the Del-1 anti-apoptotic effect was not previously known. HUVECs were assayed for cell survival by WST-8 assay following apoptotic stimuli with etoposide (FIG. 12A), TNF-α/IFNγ (FIG. 12B), or anoikis (FIG. 12C). Cells were plated in the presence of Del-1, RGD peptide or RAD peptide as a control. All experiments represent 4 repeats of each treatment group in 3 independent experiments. The presence of the RGD peptide was able to block the anti-apoptotic effect of Del-1, but not the RAD peptide as FIGS. 12A-C depict. This confirms that the RGD motif is the portion of Del1 that provides the anti-apoptotic signal.

Signaling pathways involved in Del-1's anti-apoptotic function were the focus of further analysis. As previously established, Del-1 binds integrins and integrin signaling is known to be anti-apoptotic in endothelial cells. Del-1 was shown to bind integrins via an RGD motif. In other systems, integrin signaling is known to have an anti-apoptotic effect through activation of focal adhesion kinase (FAK), which then activates a protein kinase cascade including ERK. Alahari S K, Reddig P J, Juliano R L. Biological aspects of signal transduction by cell adhesion receptors. *Int Rev Cytol* 220 (2002) 145-84.

In order to determine whether Del-1 signaling follows this molecular pathway, cell lysates from HUVECs attached to plates coated with Del-1, or with BSA as a control, and then analyzed for FAK and ERK activation. After attachment, HUVECs were harvested for total cell lysates. Equal amounts of protein were electrophoresed on SDS-PAGE, transferred to nylon membranes and subjected to immunoblotting using antibodies specific for total FAK and ERK and the phosphorylated forms of FAK and ERK. FAK and ERK show increased activation as determined by increased phosphorylation following HUVEC attachment to plates coated with Del-1 but not with BSA suggesting that Del-1 activates this signaling pathway during attachment.

The ability of Del-1 to activate FAK and ERK in HUVECs grown in suspension was then tested. Interestingly, it was determined that there is no difference in FAK and ERK activation in HUVECS grown in suspension when they are treated with Del-1 or not. This data was interpreted to suggest that another pathway was involved in mediating the anti-apoptotic effects of Del1 during anoikis. The cell lysates were then analyzed for activation of Akt, another signaling pathway involved in apoptosis. Scheid M P, Woodgett J R. PKB/AKT: functional insights from genetic models. *Nat Rev Mol Cell Biol* 2(10) (2001) 760-8. It was found that cells grown in suspension show increased activation of Akt following treatment with Del-1 and, regarding cell attachment, it was found that Akt is activated regardless of whether Del-1 or BSA is used to coat to plates. These data lead to the conclusion that Del-1 's anti-apoptotic effect is mediated by both FAK/ERK and PI3/Akt pathway activation under conditions of cell attachment to coated plates, but is mediated primarily by PI3/Akt during anoikis.

FIGS. 13A-C depicts the results of a separate method to confirm the role of FAK/ERK and PI3/Akt signaling in mediating the anti-apoptotic effect of Del-1 due to etoposide (FIG. 13A), TNF-α/IFNγ (FIG. 13B), or anoikis (FIG. 13C), the assays were repeated in the presence or absence of Del-1, a ERK kinase inhibitor (U0126), PI3 kinase inhibitor (wortmannin) or JNK kinase inhibitor (SB203580). As before, the addition of Del1 lead to decreased apoptosis as measured by WST-8 assay (FIGS. 13A-C). Addition of ERK inhibitor was capable of blocking the anti-apoptotic effects of Del-1 following treatment with etoposide or TNF-α, but not during anoikis. The addition of wortmannin, a specific inhibitor of PI3 kinase, was able to block the anti-apoptotic effects of Del-1 in response to all three triggers of apoptosis. This provides a second line of evidence suggesting that the FAK/ERK and PI3/Akt pathways are involved in the anti-apoptotic effects of Del-1 following etoposide or TNF-α exposure, but only the PI3/Akt pathway is required by Del-1 to prevent anoikis.

Example 12

Del-1 and Osteoarthritis

There is an established role for integrin biology in the development of osteoarthritis (OA). Mice that have been engineered to delete the integrin α1 gene develop normally and have no apparent joint or skeletal deformities. Integrin α1 is normally expressed in the hypertrophic and articular cartilage. However, at 9 months of age, the integrin α1 knockout mice demonstrate evidence of early arthritis when compared to wild-type controls. Zemmyo M, Meharra E J, Kuhn K, et al. Accelerated, aging-dependent development of osteoarthritis in alpha1 integrin-deficient mice. *Arthritis Rheum* 48(10) (2003) 2873-80. Histologic analysis of the joints suggests that this may be due to increased apoptosis of the chondrocytes. Finally, these transgenic mice have also been shown to heal fractures with diminished fracture callus. Ekholm E, Hankenson K D, Uusitalo H, et al. Diminished callus size and cartilage synthesis in alpha 1 beta 1 integrin-deficient mice during bone fracture healing. *Am J Pathol* 160(5) (2002) 1779-85.

Figure 14C:
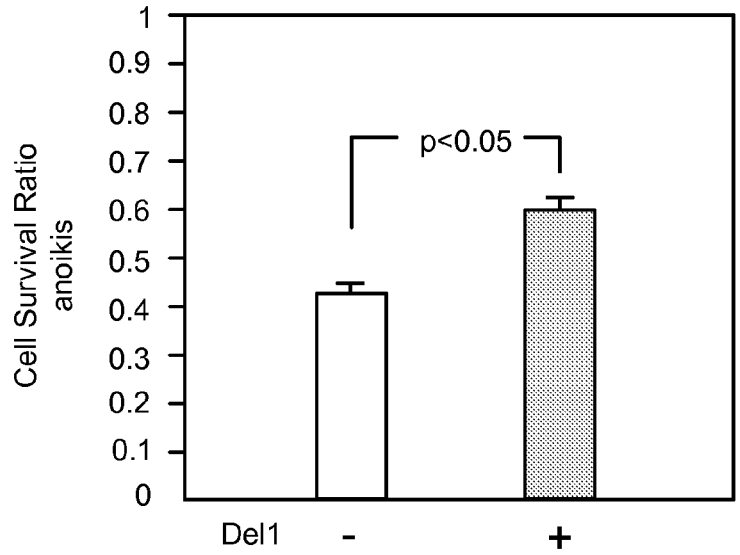

Studies were undertaken to determine a role for Del-1 in preventing apoptosis of chondrocytes. The results are depicted in FIGS. 14A-C. Primary human chondrocytes were assayed for apoptosis due to serum starvation (FIG. 14A), etoposide (FIG. 14B), and anoikis (FIG. 14C). TNF-α assays were not performed as chondrocytes are reported to not be sensitive to TNF-α induced apoptosis, as confirmed by our laboratory (data not shown). Cell death was assayed using the WST-8 assay. Statistically significant increases in the numbers of chondrocytes surviving with the addition of Del-1 were observed under all three conditions (FIGS. 14A-C). To confirm the increase in cell survival was due to decreased apoptosis, TUNEL assays were performed on cells treated with etoposide with or without Del-1. These data showed that the increase in cell survival was due to a decrease in apoptosis.

Because Del-1 is such a specific marker for cartilaginous tissues during mouse development, efforts to determine whether Del-1 is also up regulated in an in vitro model of chondrogenesis were undertaken. AdMSCs can be differentiated into structures that histologically look like cartilage with the appropriate differentiation medium. AdMSCs were harvested from wild type mice and cells from the second passage were used for differentiation. Cells are allowed to adhere into a micromass and placed into chondrogenic medium (DMEM, 1% FCS, penicillin/streptomycin, ascorbate, insulin, transferrin, insulin-like growth factor 3 (IGF3), and TGF-β1). Micromass cultures were removed at 0, 3, 6, and 9 days of culture for harvesting of total RNA, and were analyzed by quantitative real-time PCR (qPCR) for the presence of Del-1. Full chondrocytic differentiation requires 3-4 weeks in this model. By the results depicted in FIG. 15, it was determined that Del-1 is up regulated very early in differentiation to over 40-fold baseline by 9 days after placing in chondrogenic medium. For depiction of the relative expression results of FIG. 15, expression at day 0 was set to one.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

We claim:

1. A method for treating degenerative osteoarthritis comprising: reducing chondrocyte apoptosis and inducing chondrocyte differentiation at a site affected by degenerative osteoarthritis by providing a cell-free composition comprising an isolated developmental endothelial locus-1 (Del-1) protein at the site affected by degenerative osteoarthritis, thereby treating the degenerative osteoarthritis.

2. The method of claim 1, wherein the composition further comprises a carrier for prolonged release of the isolated Del-1 protein locally at the site affected by degenerative osteoarthritis.

3. The method of claim 1, wherein the isolated Del-1 protein is provided as a recombinant protein.

4. The method of claim 2, wherein the carrier is a structural scaffold material.

5. The method of claim 2, wherein the carrier is a non-structural semi-fluid material.

6. The method of claim 2, wherein the carrier is a hydrogel.

7. The method of claim 2, wherein the carrier is a polymer.

* * * * *